US011771381B2

(12) United States Patent
De Haan

(10) Patent No.: US 11,771,381 B2
(45) Date of Patent: Oct. 3, 2023

(54) DEVICE, SYSTEM AND METHOD FOR MEASURING AND PROCESSING PHYSIOLOGICAL SIGNALS OF A SUBJECT

(71) Applicant: KONINKLIJKE PHILIPS N.V., Eindhoven (NL)

(72) Inventor: Gerard De Haan, Helmond (NL)

(73) Assignee: Koninklijke Philips N.V., Eindhoven (NL)

(*) Notice: Subject to any disclaimer, the term of this patent is extended or adjusted under 35 U.S.C. 154(b) by 270 days.

(21) Appl. No.: 16/493,772

(22) PCT Filed: Feb. 27, 2018

(86) PCT No.: PCT/EP2018/054831
§ 371 (c)(1),
(2) Date: Sep. 13, 2019

(87) PCT Pub. No.: WO2018/166788
PCT Pub. Date: Sep. 20, 2018

(65) Prior Publication Data
US 2020/0121262 A1   Apr. 23, 2020

(30) Foreign Application Priority Data
Mar. 13, 2017 (EP) ..................... 17160589

(51) Int. Cl.
*A61B 5/00* (2006.01)
*A61B 5/02* (2006.01)
(Continued)

(52) U.S. Cl.
CPC .......... *A61B 5/7285* (2013.01); *A61B 5/0046* (2013.01); *A61B 5/0077* (2013.01);
(Continued)

(58) Field of Classification Search
CPC . A61B 5/0046; A61B 5/0077; A61B 5/02007; A61B 5/02416; A61B 5/0245;
(Continued)

(56) References Cited

U.S. PATENT DOCUMENTS 6,997,879 B1   2/2006 Turcott
8,740,806 B2 *  6/2014 Parfenova .......... A61B 5/02007
600/529

(Continued)

FOREIGN PATENT DOCUMENTS

WO   2016097708 A1   6/2016
WO   2016187461 A1   11/2016
WO   2016193735 A1   12/2016

OTHER PUBLICATIONS

Elgendi, Mohamed. "On the analysis of fingertip photoplethysmogram signals." Current cardiology reviews 8.1 (2012): 14-25. https://doi.org/10.2174/157340312801215782 (Year: 2012).*

(Continued)

*Primary Examiner* — Jonathan T Kuo

(57) ABSTRACT

The present invention relates to a device and method for processing physiological signals of a subject and in particular to a system for monitoring a (vascular) health parameter of a subject including such a device. The proposed device (10) comprises an input interface (11) for obtaining image data of a scene, said image data comprising a time sequence of image frames; an extraction unit (12) for extracting time-varying signals (92) indicative of cardiac-synchronous motion from said image data, wherein said time-varying signals (92) are motion signals indicative of a vascular micro-motion indicative of a vascular displacement waveform; a polarity determination (13) unit for determining a polarity of the time-varying signals, wherein the polarity corresponds to a phase of the time-varying signals; a combination unit (14) for combining time-varying depending on
(Continued)

their polarity to obtain a combination signal; and an analysis unit (15) for determining a (vascular) health parameter based on the combination signal.

17 Claims, 9 Drawing Sheets

(51) Int. Cl.
    *A61B 5/024*     (2006.01)
    *A61B 5/0245*     (2006.01)

(52) U.S. Cl.
    CPC ........ *A61B 5/02007* (2013.01); *A61B 5/0245* (2013.01); *A61B 5/02416* (2013.01); *A61B 5/7246* (2013.01)

(58) Field of Classification Search
    CPC ....... A61B 5/70; A61B 5/7246; A61B 5/7285; G06T 7/20–7/292; G06T 2207/30004–2207/30104
    USPC ......................................................... 382/107
    See application file for complete search history.

(56) References Cited

U.S. PATENT DOCUMENTS

| | | | | |
|---|---|---|---|---|
| 9,895,060 | B2* | 2/2018 | Kang | A61B 5/7285 |
| 10,080,528 | B2* | 9/2018 | DeBusschere | A61B 5/02125 |
| 10,420,470 | B2* | 9/2019 | Kwon | A61B 5/021 |
| 10,448,846 | B2* | 10/2019 | Tarassenko | A61B 5/725 |
| 10,939,852 | B2* | 3/2021 | Guazzi | G06T 7/0012 |
| 2006/0224073 | A1* | 10/2006 | Lin | A61B 5/02007 |
| | | | | 600/513 |
| 2012/0195486 | A1* | 8/2012 | Kirenko | A61B 5/02416 |
| | | | | 382/131 |
| 2013/0046192 | A1 | 2/2013 | Lin et al. | |
| 2014/0079729 | A1* | 3/2014 | Kalidindi | A61P 3/06 |
| | | | | 424/195.18 |
| 2014/0128697 | A1* | 5/2014 | Parfenova | A61B 5/0295 |
| | | | | 600/479 |
| 2014/0155759 | A1 | 6/2014 | Kaestle et al. | |
| 2015/0105638 | A1 | 4/2015 | Eisen et al. | |
| 2015/0223700 | A1 | 8/2015 | Kirenko | |
| 2015/0320363 | A1 | 11/2015 | De Haan | |
| 2015/0366492 | A1 | 12/2015 | De Haan | |
| 2017/0000350 | A1* | 1/2017 | Kwon | A61B 5/0059 |
| 2017/0007125 | A1* | 1/2017 | Kang | A61B 5/0261 |
| 2017/0249445 | A1* | 8/2017 | Devries | A61B 5/742 |
| 2017/0354334 | A1* | 12/2017 | Tarassenko | A61B 5/725 |
| 2018/0153455 | A1* | 6/2018 | Guazzi | A61B 5/02416 |
| 2018/0177464 | A1* | 6/2018 | DeBusschere | A61B 5/0077 |

OTHER PUBLICATIONS

Rubins, Uldis, et al. "Photoplethysmography analysis of artery properties in patients with cardiovascular diseases." 14th Nordic-Baltic Conference on Biomedical Engineering and Medical Physics. Springer, Berlin, Heidelberg, 2008. https://doi.org/10.1007/978-3-540-69367-3_85 (Year: 2008).*

Sievi, Noriane A., et al. "Physical inactivity and arterial stiffness in COPD." International journal of chronic obstructive pulmonary disease 10 (2015): 1891. doi: 10.2147/COPD.S90943 (Year: 2015).*

Udi Nussinovitch, The Heart in Rheumatic, Autoimmune and Inflammatory Diseases: Pathophysiology, Clinical Aspects and Therapeutic Approaches, Academic Press, 2017, ISBN 9780128032688, p. 102 (Year: 2017).*

International Search Report and Written Opinion, International Application No. PCT/EP2018/054831, dated May 4, 2018.

Dang, T. et al., "Recognizing area of pulsations on the neck via video camera systems", 2015 International Conference on Advanced Technologies for Communications, 2015.

G. de Haan and V. Jeanne, "Robust pulse-rate from chrominance-based rPPG", IEEE, Tr. On Biomedical Engineering, vol. 60, No. 10, Oct. 2013, pp. 2878-2886, PDF.DOI: 10.1109/TBME.2013.2266196.

G. de Haan and A. van Leest, "Improved motion robustness of remote-PPG by using the blood volume pulse signature", Physiol. Meas. 35 1913, 2014, PDF, DOI: 10.1088/0967-3334/35/9/1913.

M. van Gastel, S. Stuijk and G. de Haan, "Motion robust remote—PPG in infrared", IEEE, Tr. On Biomedical Engineering, 2015, DOI: 10.1109/TBME.2015.2390261.

A. Moço, S. Stuijk, and G. de Haan, "Ballistocardiographic Artifacts in PPG Imaging", IEEE, Tr. on Biomedical Engineering, vol. PP, No. 99, Nov. 2015, DOI: 10.1109/TBME.2015.2502398.

A. Moço, S. Stuijk, and G. de Haan, "Motion robust PPG-imaging through color channel mapping", Biomedical Optical Express, vol. 7, No. 5, pp. 1737-1754, May 2016, https://www.osapublishing.org/boe/fulltext.cfm?uri=boe-7-5-1737, DOI: 10.1364/BOE.7.001737.

Verkruysse, W. et al., "Remote plethysmographic imaging using ambient light", Opt Express. Dec. 22, 2008; 16(26): 21434-21445; IEEE, Tr. on Biomedical Engineering, vol. PP, No. 99, Nov. 2015.

L. Tarassenko et al., Non-contact video-based vital sign monitoring using ambient light and auto-regressive models, Physiol. Meas. 35 (2014) 807-831.

Zamani, P. et al., "Reflection Magnitude as a Predictor of Mortality: The MultiEthnic Study of Atherosclerosis", Hypertension. Nov. 2014; 64(5): 958-964.

Townsend, R. et al., "American Society of Hypertension position paper: central blood pressure waveforms in health and disease", ASH Position Paper, Journal of the American Society of Hypertension, 10(1), 2016, 22-23.

Hametner, B. et al., "Wavereflectionquantificationbasedonpressure waveformsalone—Methods,comparison, andclinicalcovariates", Computer Methods and Programs in Biomedicine 109 (2013).

Hughes, A. et al., "Forward and backward waves in the arterial system: impedance or wave intensity analysis?", Med Biol Eng Comput (2009) 47: 207-210.

* cited by examiner

DEVICE, SYSTEM AND METHOD FOR MEASURING AND PROCESSING PHYSIOLOGICAL SIGNALS OF A SUBJECT

CROSS-REFERENCE TO PRIOR APPLICATIONS

This application is the U.S. National Phase application under 35 U.S.C. § 371 of International Application No. PCT/EP2018/054831, filed on 27 Feb. 2018, which claims the benefit of European Patent Application No. 17160589.2, filed on 13 Mar. 2017. These applications are hereby incorporated by reference herein.

FIELD OF THE INVENTION

The present invention relates to the field of medical technology and in particular to a device for processing physiological signals of a subject as well as a corresponding method and computer program. The present invention further relates to a corresponding system for monitoring a health parameter of a subject.

BACKGROUND OF THE INVENTION

Different techniques exist for cardiovascular health assessment such as computer tomography (CT) imaging using contrast agents, magnetic resonance imaging, calibrated applanation tonometry, ultrasound imaging or laser Doppler velocimetry (LDV). All of these techniques require dedicated equipment and a well-trained operator. For example, LDV requires users to manually find the optimal spot for data acquisition and manually adjust the laser beam, a task which is fastidious and error prone.

Dang et al., "Recognizing area of pulsations on the neck via video camera systems", International Conference on Advanced Technologies for Communication (ATC), p. 139-144, 2015, discloses a camera-based system for detecting an area of pulsations on a patient's neck. The paper thus describes a system and method for non-contact identification of an area of pulsation. Areas of pulsation are determined and marked for the physician. In order to further improve the system, Dang et al. suggest the use of a depth camera since it is held that the estimation of the pulsating area is much easier with depth frames created from a depth camera (3D camera) instead of using a video camera.

WO 2016/187461 A1 relates to optical central venous pressure measurement. A computer-implemented method is presented comprising: capturing a video of a person's neck; processing the captured video according to one or more video motion amplification techniques by one or more computing devices to generate a reconstructed video in which pulsatile motion of the person's venous system that occurs in the person's neck is amplified; measuring, by the one or more computing devices, a distance between a peak of the amplified pulsatile motion and an anatomical feature of the person; and determining central venous pressure (CVP) of the person by the one or more computing devices based on the measured distance for the amplified pulsatile motion.

WO 2016/097708 A1, US 2013/0046192 A1 and US 2014/0155759 A1 on the other hand relate to the different approach of remote PPG wherein a time-varying absorption caused by chromophores, such as oxygenated and de-oxygenated hemoglobin, is evaluated.

SUMMARY OF THE INVENTION

It is an object of the present invention to provide a device, system and method which enable improved remote determination of a health parameter, in particular indicative of a vascular health of a subject.

According to a first aspect of the present invention a device for processing physiological signals of a subject is presented, the device comprising:
an input interface for obtaining image data of a scene, said image data comprising a time sequence of image frames;
an extraction unit for extracting time-varying signals indicative of cardiac-synchronous motion from said image data, in particular, wherein said time-varying signals are motion signals indicative of a vascular micro-motion indicative of a vascular displacement waveform;
a polarity determination unit for determining a polarity of the time-varying signals, in particular, wherein the polarity corresponds to a (relative) phase of the time-varying signals;
a combination unit for combining time-varying signals depending on their polarity to obtain a combination signal; and
an analysis unit for determining a health parameter based on the combination signal.

In a further aspect of the present invention a method for processing physiological signals of a subject is provided. The method comprises the steps of:
obtaining image data of a scene, said image data comprising a time sequence of image frames;
extracting time-varying signals indicative of cardiac-synchronous motion from said image data, in particular, wherein said time-varying signals are motion signals indicative of a vascular micro-motion indicative of a vascular displacement waveform;
determining a polarity of the time-varying signals, in particular, wherein the polarity corresponds to a (relative) phase of the time-varying signals;
combining time-varying signals depending on their polarity to obtain a combination signal; and
determining a health parameter based on the combination signal.

According to yet another aspect of the present invention, a system for monitoring a health parameter of a subject is presented, the system comprising
an imaging unit for acquiring image data of a scene; and
a device as described above for processing physiological signals of a subject, based on the acquired image data of the scene. The health parameter can in particular be a vascular health parameter indicative of a vascular health or state of the subject.

In further aspects of the present invention, there are provided a computer program which comprises program code means for causing a computer to perform the steps of the method disclosed herein when said computer program is carried out on a computer, as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and non-transitory computer-readable recording medium can have similar and/or identical preferred embodiments as the claimed device and as defined in the dependent claims.

The herein presented solutions provide a possibility to enable a more reliable and/or accurate determination of a health parameter, in particular a vascular health parameter indicative of a vascular health or state of the subject.

The present invention is based on the idea of determining a (relative) polarity of time-varying signals indicative of cardiac-synchronous motion, combining time-varying signals depending on their polarity to obtain a combination signal, and determining a health parameter based on the combination signal.

It has been found that a vascular displacement waveform, e.g. indicative of a displacement of a carotid artery, can provide valuable information regarding the vascular system. As the displacement waveform closely resembles the (aortic) central pressure waveform, its assessment is recognized as an opportunity for improving cardiovascular risk stratification. The displacement waveform, and more specifically the morphology thereof, can yield valuable information of the (vascular) health of the subject. Vascular displacement can translate to (micro)-motion on the skin of the subject that can be observed non-obtrusively. An imaging unit such as a conventional camera can thus acquire time-varying signals indicative of cardiac-synchronous (micro)-motion that is indicative of a vascular displacement waveform such as a carotid artery displacement waveform.

The inventor has recognized that such time-varying signals that are indicative of a cardiac-synchronous (micro)-motion provide a peculiar distribution that can be used to improve the system performance. While photoplethysmographic (PPG) signals indicative of cardiac-synchronous absorption always have the same polarity over a region of interest, it has been found that this is not true for time-varying signals indicative of cardiac-synchronous (micro)-motion. To the contrary, motion may increase the amount of reflected light that is seen by the imaging unit in a first region of the image, while at the same time decreasing the amount of reflected light that is seen by the imaging unit in a second region of the image. In particular under inhomogeneous lighting conditions such as illumination of the skin of a subject under an oblique angle, a vascular displacement, e.g. due to carotid artery displacement, may slightly lift a skin region such that it provides a small elevation or bump on the surface. One side of said elevation is brightly illuminated, whereas the other side is shadowed. A cardiac-synchronous rising and falling motion of such an elevation thereby leads to a cardiac-synchronous intensity variation in the image data captured by the imaging unit wherein the two sides of the elevation can have opposite polarity. By taking into account the polarity of the time-varying signals indicative of cardiac-synchronous motion when combining signals, the quality of a resulting combination signal can be improved with the associated benefits in terms of reliability and/or accuracy. Simply combining time-varying signals without taking the polarity into account may actually decrease a signal-to-noise ratio of an acquired combination signal. In extreme cases, the signals of opposite polarity may cancel out completely in the combined signal.

As indicated above, PPG signals always have the same polarity. PPG is an absorption-based technique that relies on the principle that blood absorbs light more than surrounding tissue for most wavelengths. In the context of PPG, Verkruysse et al., "Remote plethysmographic imaging using ambient light", Optics Express, 16(26), 22 Dec. 2008, pp. 21434-21445 demonstrate that photoplethysmographic signals can be measured remotely using ambient light and a conventional consumer level video camera. The absorption variation of the time-varying signals of different pixels of an image is in phase since it is caused by measuring absorption (variations) caused by chromophores in the tissue (typically blood). The polarity or phase of absorption-based signals, occurring at spatially neighboring locations is substantially the same. In PPG imaging, it is known that a motion of the monitored subject may affect the PPG signal. Therefore, the prior art in PPG imaging considers motion as an unwanted contribution that has to be eliminated.

Instead of treating motion signals simply as artifacts that should be suppressed, the inventor follows a different approach in that cardiac-synchronous (micro)-motions are used for determining a (vascular) health parameter. In particular, it has been recognized that vascular volume/skin displacements may cause some areas of the skin surface to influence the reflected light in one direction whereas other areas may influence the reflected light in opposite direction. To further improve the quality of a resulting combination signal, it is not sufficient to simply combine pixels having a sufficiently strong signal amplitude, but the phase or polarity has to be taken into account.

During operation, the imaging unit for acquiring the image data shall be directed to register a tissue region of the subject including a portion with a (superficial) artery such as the carotid, radial, femoral artery, or the like.

The image data comprising a time sequence of image frames can correspond to data acquired with a two-dimensional array of pixels, as for example acquired using an image sensor in conventional video cameras. However, it may also refer to data acquired with different arrangement of photo sensors such as line-array, or even a single photo-sensor combined with a scanning technique. The term image data as consistently used herein, can thus also refer to data acquired by a 1D-pixel array, e.g. when using a line-sensor without scanning. In general, the image data is provided by multiple photo-sensors representing different parts of the scene. A time-varying signal can be indicative of or correspond to a pixel in the image data. Image data as used herein refers to data representing electromagnetic (EM) radiation reflected, at least in part, from the skin of a subject. This data has been acquired by one or more sensors and the one or more sensors are sampled (regularly) in time, so as to obtain time-sequences (signals) from every sensor representing different parts of the scene. This applies mutatis mutandis to single sensor combined with a scanning technique. Additional pre-processing such as rescaling, resampling, selection of regions within the image data and/or tracking and overall body motion of the subject can be applied. In case the sensor samples the scene irregularly, the data may be resampled to a regular sampling pattern prior to further processing.

The (relative) polarity of the time-varying signals can be thought of as a phase of the time-varying signals at the frequency of a periodic physiological phenomenon, for example at the heart rate of the subject. The absolute phase or polarity is not required to be known since it is the relative polarity or phase of time-varying signals with respect to each other based on which the signals are combined by the combination unit.

The combination unit can combine signals having the same polarity but it is also possible to combine the time-varying signals from a plurality of pixels by adjusting, in particular by inverting the polarity of some of the time-varying signals such that all the time-varying signals contributing to the combination signal have the same polarity. Hence, even if the absolute polarity of the time-varying signals is not known, the polarity determination unit may still compare their relative polarity or phase relationship which is then taken into account by the combination unit. Thereby, the signal-to-noise ratio can be further improved.

The time-varying signals are motion signals indicative of a vascular micro-motion. Hence, in contrast to a remote PPG measurement the time-varying signals are not absorption-based signals indicative of a time-varying absorption caused by chromophores in the tissue. In an embodiment, the time-varying signals can represent an AC-part of the reflected light signals acquired by the imaging unit, where this AC-part is induced by vascular micro-motion. Light is modulated by the varying orientation of the skin relative to the light-source.

In an embodiment the extraction unit can be configured to extract the time-varying signals from a red and/or blue color channel of the image data only. In this embodiment, the image data can advantageously be data acquired by an RGB-camera. An advantage of this embodiment is that it is less sensitive to cardiac-synchronous absorption variations. In particular, blood does not strongly absorb the red light. Advantageously the green channel is not used since it is most sensitive to cardiac-synchronous absorption variations. Thereby, absorption-based artifacts can be reduced or even eliminated.

When using the red and/or blue channel, it is further advantageous to use an illumination unit configured to emit (spectrally relatively pure) red and/or blue light, such as an LED at 660 nm or at 450 nm, since the camera channels can have a rather large range of sensitivity, i.e. the blue and red channels may still be partially sensitive to green light if present). In an embodiment, an illumination unit can be configured to emit light red light comprising a wavelength of 660 nm or 450 nm and having a FWHM (full width at half maximum) of no more than 80 nm, preferably no more than 60 nm, preferably no more than 40 nm.

In an embodiment, the extraction unit can be configured to extract time-varying signals from image data indicative of electromagnetic radiation in a wavelength interval that contains at least one of wavelengths longer than 610 nm and wavelengths shorter than 500 nm. In addition or in the alternative an opaque (but flexible) layer can be applied to the skin, e.g. sprayed on or stuck onto the skin. Thereby, absorption-based artifacts can be reduced or even eliminated, and other than the indicated wavelengths can also be used.

In an embodiment, the device can further comprise a selection unit for selecting time-varying signals corresponding to a region of interest (ROI) in the image frames of the image data; and the combination unit can further be configured to combine said selected time-varying signals from said region of interest. In particular, the selection unit can be configured to select the ROI as a first region providing signals of same polarity and being adjacent to a second region providing signals of opposite polarity. An advantage of this embodiment is reliable identification of a region indicative of vascular motion. It has been found that a vascular motion can cause both a first region to provide signals having a first polarity as well as cause a second region to provide signals having a second, opposite polarity. Thereby, a skin-area where vascular micro-motion occurs can be found. In addition or in the alternative, selecting a region of interest can include searching for the time-varying signals with the highest amplitude (which may include signals of different polarities), or providing a manual ROI (pre-)selection e.g. to limit processing requirements. Based on a manual pre-selection a further search can then be performed by the selection unit for the most pulsatile pixels followed by a determination of the polarity. In a refinement, a largest area of image signals having same polarity can be selected. Optionally, one or more additional selection criteria such as an amplitude above a predetermined threshold, minimum size of the region providing same polarity and/or size of the region providing opposite polarity may be applied. Advantageously, a group of time-varying signals or pixels most affected by vascular motion, i.e. due to the pulse wave in superficial artery, are thus selected. In the selection of pixels, additionally the quality of the motion-induced signal may be judged by the waveform, or any other criteria in addition to polarity.

In an embodiment the polarity determination unit is configured to correlate the time-varying signals with a signal indicative of a pulse (or pulse rate) of the subject. Thereby, a (relative) polarity or phase at the pulse rate or frequency can be determined. The signal indicative of the pulse of the subject can provide an (external) reference signal with which the motion-based time-varying signals are correlated. In a refinement the determination unit can comprise a mixer for correlating or mixing the time-varying signals with the signal indicative of the pulse of the subject. The signal indicative of the pulse can be provided externally, e.g., obtained via a (contact-based) pulse-oximeter, from an electro-cardiogram (ECG) or the like. The reference signal can be a pulse-signal, or a signal derived from a pulse-signal. The signal can look like a PPG-pulse or can be a sinusoid with the pulse-rate as obtained from a PPG or ECG-sensor. In principle any pulse-frequent signal can be used and the waveform is not very relevant. An advantage is high reliability. Alternatively or in addition the signal indicative of the pulse of the subject can be based on a PPG signal, in particular based on a PPG signal derived from the image data. In an embodiment the green color channel can be used for determining a PPG pulse signal, whereas the red color channel is used for extracting the time-varying signals indicative of cardiac-synchronous motion. Alternatively, polarity can be determined by correlation of time-varying signals with respect to each other, which advantageously does not require an external reference.

In a further refinement, the signal indicative of a pulse of the subject is derived from a photoplethysmographic (PPG) signal or an electrocardiographic (ECG) signal. Advantageously, the PPG signal can be extracted from the image data. For example when observing a motion from the carotid artery, a PPG signal can be extracted from a chin or cheek region which is only little effected by pulsatile motion. It shall be understood that other areas can be chosen when observing a motion from other vessels. Advantageously, the signal indicative of the pulse of the subject is a Hilbert transformed (PPG) signal. In particular in case of using ECG, the signal can be processed to remove higher harmonics by a low-pass filtering before using the signal for correlation.

In an embodiment the health parameter can be a vascular health parameter comprising at least one of a stiffness index, an augmentation pressure, an augmentation index and a reflection magnitude. An advantage of this embodiment is that specific information regarding a vascular health state of the subject is provided. The vascular health parameter can be calculated from the shape of the combination signal. The afore-mentioned parameters can be defined by the following equations:

stiffness index: $SI = h/TD_{fp}$, augmentation index: $ALx = (1 - \max(D_f)) \cdot 100(\%)$ augmentation pressure: $AP = AIx \cdot (SBP - DBP)$ reflection magnitude:

$$RM = \frac{\max(D_b)}{\max(D_f)} \cdot 100(\%)$$

where h is the subject's height, $TD_{fr}$ is the temporal delay between forward and reflected waves, $D_f$ and $D_b$ denote the forward and backward waveform decompositions of an exemplary time-varying signal indicative of a carotid displacement waveform $D_{CA}$, SBP and DBP denote the Systolic Blood Pressure and Diastolic Blood Pressure, respectively. Details of the parameters are described in Zamani et al., "Epidemiology/population reflection magnitude as a predictor of mortality—the multi-ethnics study of arteriosclerosis, epidemiology, pp. 958-964, 2014, and Townsend et al. "Central blood pressure waveforms in health and disease", American Society of Hypertension Position Paper, Journal of the American Society of Hypertension 10(1): 22-33, 2016.

In an embodiment the analysis unit can be configured to derive the health parameter based on the motion-based (combination) signal and an absorption-based photoplethysmographic (PPG) signal, in particular based on a transfer function between the motion-based (combination) signal and the photoplethysmographic (PPG) signal. Hence, a relation between the motion-based signal and the absorption-based signal can be evaluated in order to derive a health parameter. For example, both signals can be derived from the image data wherein e.g. a green color channel is indicative of the PPG signal and a red color channel is indicative of the motion signal. In addition or in the alternative the motion signal and the PPG signal can also be derived from different locations within the image data, for example a PPG signal can be derived from a cheek of the subject, whereas the motion signal is measured in the vicinity of the carotid artery. The signals may also be measured at closely neighboring locations using differently colored light preferably measured in the vicinity of a major artery such as the carotid artery. A delay between the motion-based combination signal and the PPG signal can be evaluated. The delay may be used similar to or as a replacement of the pulse-transit time (PTT) which is another indicator of vascular health and related to blood pressure.

Referring now to the system for monitoring a health parameter of the subject, in an embodiment the system may further comprise an illumination unit, wherein the illumination unit and the imaging unit are arranged such that an angle φ between light emitted by the first illumination unit and light received by the imaging unit is preferably |φ|≥45°, in particular |φ|≥60°. An advantage of the proposed arrangement of imaging unit and the first illumination unit is that it enhances the visibility of micro-motions due to pulsation due to lateral/uneven lighting conditions. In particular, the first illumination unit can be arranged perpendicular to an orientation of the imaging unit. In other words, the light source can preferably be arranged such that light emitted by the light source can illuminate a region of interest on the skin of a subject under an oblique angle, in particular with respect to an optical axis or line of sight of the imaging unit. The angle φ can also refer to an angle between light emitted by the first illumination unit and a surface normal of the skin of the subject in a region of interest for acquisition of the time-varying signals. In order to evaluate micro-motions the orientation of the light surface relative to the skin-normal has been found to be highly relevant. Advantageously, the first illumination unit has an orientation almost parallel to the skin of the subject or almost 90° with respect to the skin-normal of the subject. The imaging unit should advantageously be perpendicular to the skin surface of the patient or parallel to the skin-normal. In contrast to PPG measurements in the prior art, wherein an illumination under an oblique angle has detrimental effects, it is desirable for the present system to maximize motion sensitivity. In other words, an angle between an optical axis or line of sight of the imaging unit and a primary emission direction of the first illumination unit should be 90°±45°, in particular ±30°. Perpendicular or orthogonal as used herein may refer to an angle of 90°±45°, in particular ±30°. Parallel may refer to an angle of 0°±30°, preferably ±20°. In PPG imaging, illumination under an oblique angle causes the system to become very error-prone due to increased motion sensitivity and is thus to be avoided in PPG.

In a further refinement the system may further comprise a second illumination unit, wherein the second illumination unit and the imaging unit are arranged such that an angle θ between light emitted by the second illumination unit and light being received by the imaging unit is preferably |θ|≤30°, in particular |θ|≤20°. In particular, the second illumination unit can be arranged parallel to an orientation of the imaging unit. Hence, the first illumination unit can be arranged to provide lateral illumination of a region of interest whereas the second illumination unit can be arranged to provide orthogonal illumination of a region of interest. The angle θ can also refer to an angle between light emitted by the second illumination unit and a surface normal of the skin of the subject in a region of interest for acquisition of the time-varying signals. It shall be understood that during operation the system can be arranged in a predetermined orientation with respect to the skin of the subject since determination of health parameters, in particular of vascular health parameters, is a measurement usually carried out with consent of cooperative subjects. In an embodiment, the second illumination unit may be configured to provide filling light, since some portion so of the skin may be completely shaded. Hence, portions of the skin being under low brightness may translate to sensor noise when applying AC/DC normalization. Alternatively, this problem may be circumvented, by adding a little bias to the pixel-values prior to normalization. Hence, the provision of additional filling light may decrease effects of sensor noise. In addition or in the alternative, the first illumination unit can be used to obtain time-varying signals indicative of cardiac-synchronous motion of the skin, whereas the second illumination unit can be used to obtain time-varying signals indicative of blood absorption.

In an embodiment the first light source can be configured to emit light at a first wavelength providing low absorption in blood and/or providing a shallow skin penetration depth, in particular at a wavelength shorter than 500 nm or longer than 610 nm. For example, the first light source can be configured to emit red light which helps to decrease the sensitivity for absorption variations since blood has low red-absorption. Alternatively or in the addition, blue light can be used for example at a wavelength of 450 nm which provides a low penetration depth due to a high scattering and thereby minimizes PPG pollution. Even though blue light around 450 nm is highly absorbed by blood, but does not significantly penetrate the skin. As a consequence it will hardly show any PPG signal at all.

In an embodiment the second light source can be configured to emit light at a second wavelength providing high absorption in blood, in particular a wavelength between 500 nm and 610 nm, in particular between 520 nm and 590 nm. Advantageously the second wavelength should also enable penetration into the skin. Advantageously, the acquired signal corresponding to illumination at this second wavelength is then dominated by blood-volume variation in the skin and the respective absorption-variation. Advantageously green light at a wavelength between 520 nm and 590 nm can be used. Light at the wavelengths around 550 nm penetrates the skin and is highly absorbed by blood. As a consequence the PPG signal is highest around such wavelengths.

BRIEF DESCRIPTION OF THE DRAWINGS

These and other aspects of the invention will be apparent from and elucidated with reference to the embodiment(s) described hereinafter. In the following drawings

DETAILED DESCRIPTION OF EMBODIMENTS

Figure 1:
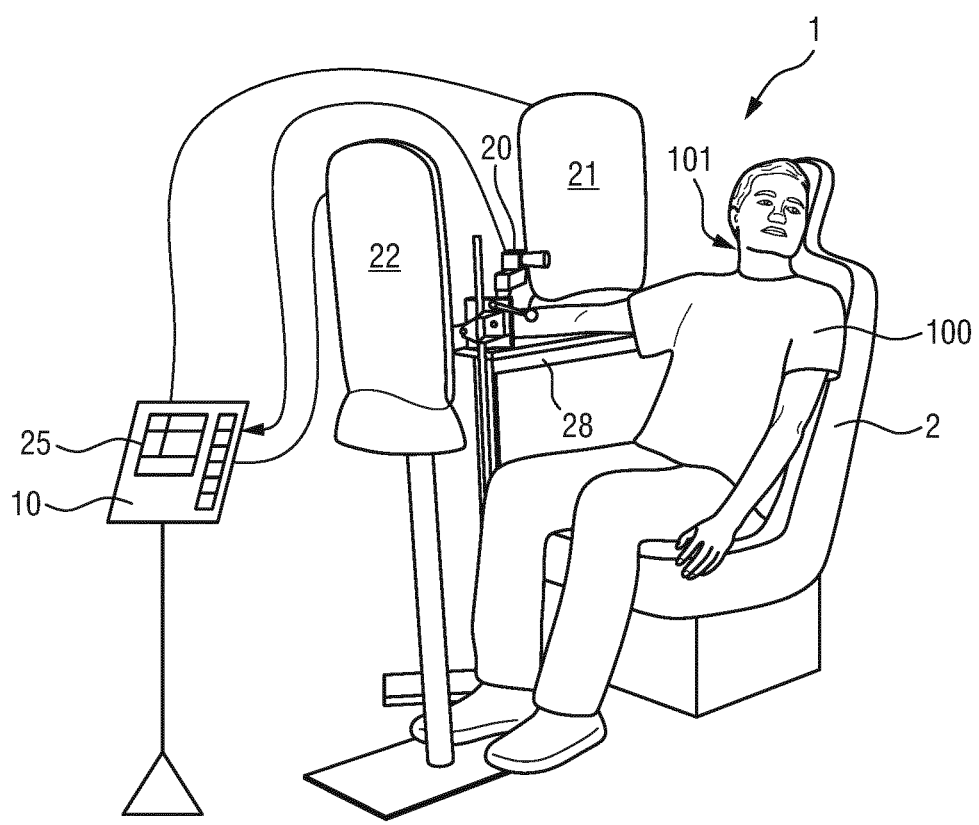
FIG. 1 shows a schematic diagram of a first embodiment of a system according to an aspect of the present invention.

FIG. 1 shows a schematic diagram of a system 1 according to an aspect of the present invention including a device 10 for processing physiological signals of the subject 100. The system 1 and device 10 may preferably be used in a method for processing physiological signals of the subject 100 from image data including a time sequence of image frames of the subject 100. The subject 100, in this example a patient, is seated in a reclined chair 2, e.g. in a hospital or other healthcare facility or at home or in a different environment such as a fitness environment. The imaging unit 20 may comprise a camera (also referred to as detection unit) for acquiring image data of the scene, in particular for acquiring a sequence of image frames of the subject 100 over time, preferably including a skin area 101 of the subject 100 from which time-varying signals indicative of cardiac-synchronous motion can be derived. In an application of the device 10, the skin area 101 is preferably in a neck area such as the right side of the neck comprising skin portions in the vicinity of the carotid artery but may also be another area of the body of the subject with a visible skin surface and being affected by cardiac-synchronous motion such as e.g. a palm region of a hand of the subject.

Figure 2:
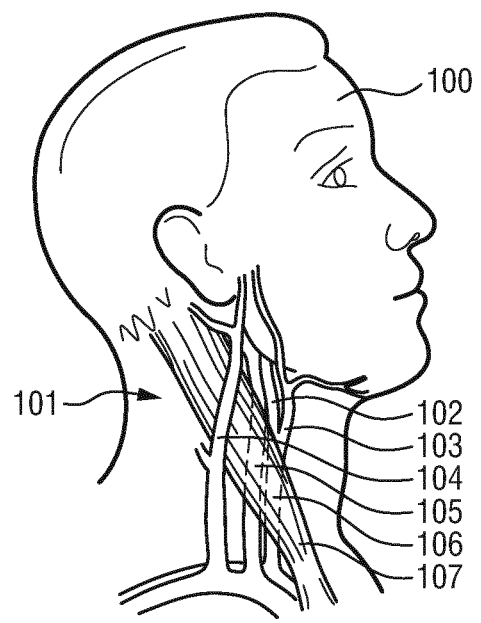
FIG. 2 shows a schematic diagram of the neck anatomy including the carotid artery.

An exemplary scene to be imaged by the imaging unit is shown in FIG. 2. Therein, a side view of the head and neck head region 101 of the subject 100 is shown. Several underlying anatomical features are also illustrated therein such as the internal carotid artery 102, the external carotid artery 103, the external jugular vein 104, the internal jugular vein 105, the common carotid artery 106 as well as the sternocleidomastoid muscle 107.

An exemplary use case of the present invention is deriving a carotid displacement waveform as the time-varying signal indicative of cardiac-synchronous motion from the image data acquired by the imaging unit 20. The carotid displacement waveform morphology provides valuable information regarding the arterial system. As the displacement waveform closely resembles the (aortic) central pressure waveform, its assessment is recognized as an opportunity for improving cardiovascular risk stratification. Of particular interest is the derivation of vascular parameters pertaining to arterial stiffness and wave reflection magnitude. It has been found that the arterial stiffness can be derived by measuring aortic pulse wave velocity (PWV) from a single waveform. Likewise, the central orientation index (AIx) and pulse pressure were found to be independent predictors of all caused mortality, while the reflection magnitude (RM), defined as the ratio of the backward and forward waves, is a valuable component to PWV for predicting heart failure. The parameters will be explained in more detail further below.

Since the carotid artery is a distensible vessel, its diameter and internal pressure are closely related over the physiological range. The cardiac-related skin motion results in time-varying signals indicative of said cardiac-synchronous motion (sMOT) that can be observed at the vicinity of the carotid artery. It has been found that such a time-varying signal can be taken as a close surrogate of the central pulse to the extent that: Carotid vessel wall movements are transmitted to the overlying skin without significant damping from subcutaneous fat and connective tissue. Hence, it is suggested to determine a (vascular) health parameter based on a time-varying signal indicative of a cardiac-synchronous motion that can be extracted from image data.

It has been found that it is feasible to acquire carotid displacement measurements by imaging the neck of a subject 100 with an imaging unit 20 such as a regular RGB-camera.

The image frames captured by the imaging unit 20 may particularly correspond to a video sequence captured by means of an analog or digital photo-sensor, e.g. in a (digital) camera. Such a camera usually includes a photo-sensor such as a CMOS or CCD sensor, which may also operate in a specific spectral range of electromagnetic radiation (visible, nIR) or provide information for different spectral ranges, particularly wavelengths advantageous for undisturbed acquisition of cardiac-synchronous motion and optionally also for enabling the extraction of photoplethysmography (PPG) signals. The camera may provide an analog or digital signal. The image frames include a plurality of image pixels having associated pixel values. A time-varying signal can be extracted separately for each pixel, for some of the pixels or also for one or more groups of pixels. Particularly, the image frames include pixels representing the light intensity values captured with different photosensitive elements of a photosensor. These photosensitive elements may be sensitive in a specific spectral range (i.e., representing a specific color such as RGB). The image frames include at least some image pixels being representative of a skin portion of the person. Thereby, an image pixel may correspond to one photosensitive element of a photo-detector and its (analog or digital) output or may be determined based on a combination (e.g. through binning) of a plurality of the photosensitive elements.

The system 1 may further include a first illumination unit 21. The first illumination unit 21 can be configured to emit light at a first wavelength providing low absorption in blood and/or providing a shallow skin presentation depth. The first illumination unit 21 can be arranged to provide lateral illumination. Depending on the angle of the skin with respect to the orientation of the illumination unit 21 a cardiac-synchronous motion of the skin for example on top of the carotid artery, translates into intensity variations due to pulsating skin asides in the image data.

Figure 3:
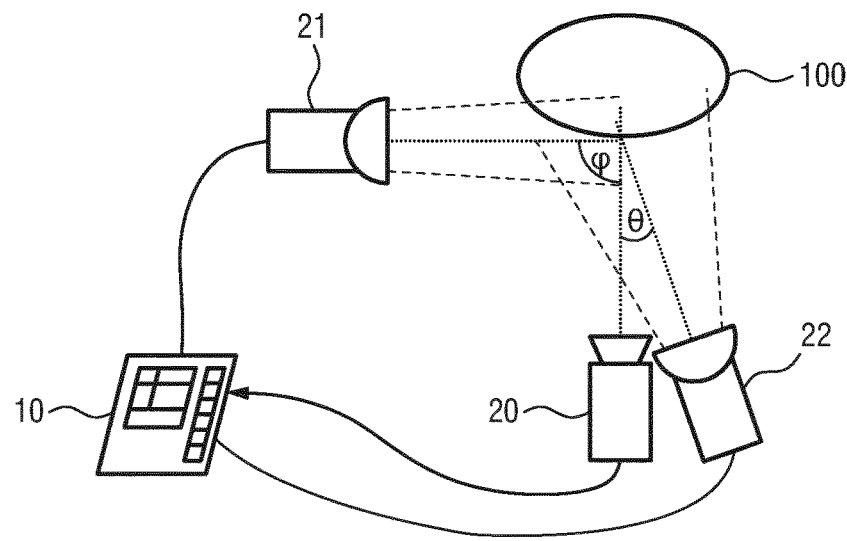
FIG. 3 shows a schematic diagram of a top view of the arrangement of the components of a second embodiment of a system.

FIG. 3 illustrates a schematic diagram of a top view of an embodiment of a system 1 for monitoring a health parameter of the subject. The first illumination unit 21 and the imaging unit 20 are preferably arranged such that an angle φ between light emitted by the first illumination unit and light received by the imaging unit is $|\varphi| 45°$, in particular $|\varphi| \geq 60°$. Uneven lighting of the moving skin at the vicinity of the carotid artery boosts brightness variations acquired by a camera. As shown in FIG. 3, the first light source 21 is preferably arranged substantially perpendicular to an orientation of the imaging unit 20. The first illumination unit 21 should have a small angle with respect to the skin normal, i.e. provide lateral illumination under an oblique angle.

As shown in FIGS. 1 and 3, the system may optionally further comprise a second illumination unit 22. The second illumination unit 22 and the imaging unit 20 are preferably arranged such that an angle θ between light emitted by the second illumination unit and light being received by the imaging unit is $|\theta| \leq 30°$, in particular $|\theta| \leq 20°$. As shown in FIG. 3, the second illumination unit 22 is preferably arranged substantially parallel to an orientation of the imaging unit 20. It shall be understood that the illumination units 21, 22 and the imaging unit 20 can be all arranged in the same plane or in different planes.

The first illumination unit 21 is preferably configured to emit light at a first wavelength providing low absorption in blood and/or providing a shallow skin penetration depth such as red light at a wavelength of 650 nm and/or blue light at a wavelength of 450 nm. For example, video recordings performed in a red wavelength get a much larger contribution from the desired carotid displacement signal, $D_{CA}$, as the time-varying signal. An absorption-based contribution in the red color channel has been found to have the lowest strength among the visible-to-infrared spectrum.

The second illumination unit 22 is preferably configured to emit light at a second wavelength providing high absorption in blood. For example, light can be emitted at a wavelength of or around 550 nm, i.e. green light. This light penetrates the skin and is highly absorbed by blood. As a consequence, a PPG signal having a strong amplitude can be obtained at this second wavelength, whereas a motion-signal having strong amplitude can be obtained at the first wavelength. In addition or in the alternative, the second illumination unit may also provide filling light as described above.

The illumination units 21, 22 can also be referred to as illumination sources or light sources or electromagnetic radiators. The illumination units may comprise a lamp or LED for illuminating/irradiating a region of interest 101 of the subject 100 with light, for instance in a predetermined wavelength range or ranges as described above. The light reflected from the region of interest 101 in response to said illumination is detected by the camera 20. In another embodiment no dedicated light source is provided, but ambient light is used for illumination of the subject 100. From the reflected light only light in a desired wavelength range or ranges for example green and red or infrared light may be detected and/or evaluated by the device 10. The imaging unit 20 is connected to the device 10 wired or wirelessly. Furthermore, image data provided by the imaging unit 20 can be stored locally or remotely and may be processed by the device 10 at the same or at a later point in time and/or at the same location as the subject or at a remote location.

The device 10 can be further connected to an interface 25 for displaying the determined information and/or for providing medical personnel with an interface to change settings of the device 10, the imaging unit 20, the first illumination unit 21, the second illumination unit 22 and/or other parameters of the system 1. Such an interface 25 may comprise different displays, buttons, touchscreens, keyboards or other human machine interface means.

The uni- or bi-directional communication between the device 10, the imaging unit 20, the interface 25 and optionally also one or more of the first and second light source 21, 22 may work via a wireless or wired communication interface. Other embodiments of the present invention may include a device 10, which is not provided stand-alone, but integrated into the imaging unit 20 or the interface 25.

Figure 4:
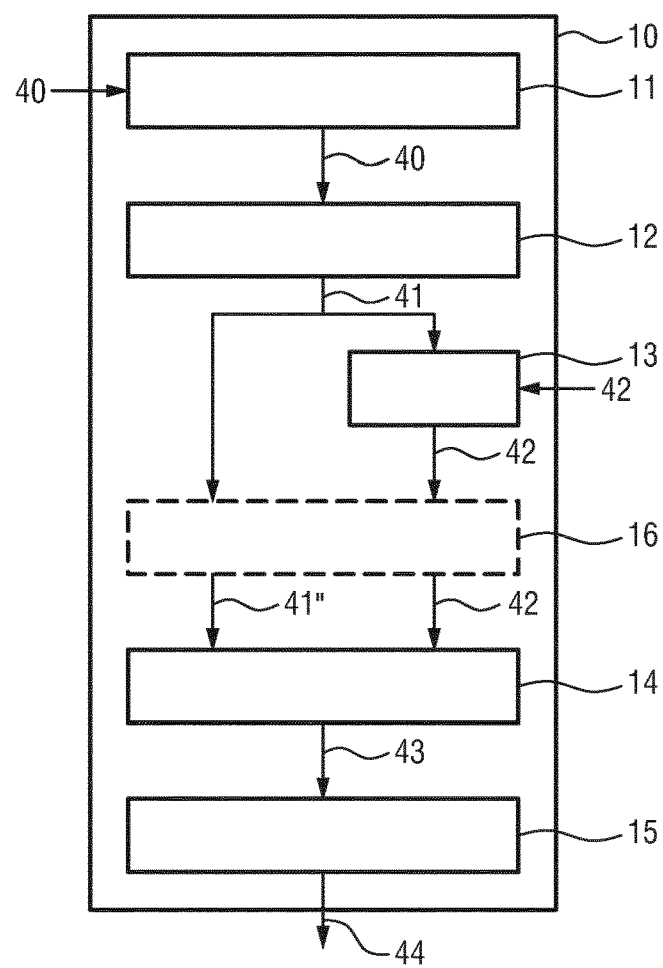
FIG. 4 shows a schematic diagram of a first embodiment of a device according to an aspect of the present invention.

FIG. 4 shows a first schematic diagram of a first embodiment of a device 10 according to an aspect of the present invention which may be used as the device 10 in the system 1 shown in FIG. 1 or 3. The device 10 for processing physiological signals of the subject 100 comprises an input interface 11 for obtaining image data 40 of a scene such image data comprising a time sequence of image frames. The image data can be received or retrieved by the device 10. For example, the image data can be received from an imaging unit 20 via a wired or wireless interface or can be retrieved from a data source such as a cloud based storage or server. The time-varying signals 41 can be motion signals indicative of a vascular micro-motion. An extraction unit 12 extracts time-varying signals 41 indicative of cardiac-synchronous motion from the image data 40. Individual time-varying signals can correspond to respective time sequences of individual pixels of the image frames. A time-varying signal may also be derived from a group of (neighboring) pixels or an area resulting from a segmentation of one or more image frames. Advantageously, the extraction unit is configured to extract the time-varying signals 41 from a red color channel of the image data for example in case the image data is provided by a conventional RGB-camera. A polarity determination unit 13 then determines a polarity of the time varying signals 41.

The polarity determination unit 13 can be configured to correlate the time-varying signals 41 with a signal 42 indicative of a pulse of the subject 100. The pulse of the subject can preferably be derived from the image data using known PPG techniques in particular using the green channel of image data provided by an RGB-camera. In addition or in the alternative the pulse signal may be provided externally as indicated in FIG. 4, for example from a (filtered) ECG measurement or from a pulse-oximeter. The (relative) polarity or phase of the time-varying signals 41 can thereby be determined. However, it is also possible to determine a relative polarity of the time-varying signals based on a spectral analysis of one or more time-varying signals themselves, for example by means of a fast Fourier transform or the like and comparing the time-varying signals among each other.

A combination unit 14 then combines time-varying signals depending on their polarity to obtain a combination signal 43. Information about the polarity of the time-varying signals can be provided from the polarity determination unit 13 as a polarity signal 42. Finally, an analysis unit 15 determines a (vascular) health parameter based on the combination signal 43 which can then be provided as an output of the device 44. Referring again to FIG. 1, the result can be shown on a human machine interface 25.

The signals 41 and 42 can be directly provided to the combination unit 14. In the embodiment shown in FIG. 4, an optional selection unit 16 is provided. The selection unit 16 can be configured to select time-varying signals 41 corresponding to a region of interest (ROI) in the image frames of the image data, in particular as a region providing signals of same polarity and being adjacent to a region providing time-varying signals of opposite polarity. The combination unit can be further configured to combine said selected time-varying signals 41' form said region of interest.

The selection unit 16 may further take the signal 42 indicative of a pulse of the subject 100 into account. For example the selection can be based on an amplitude of the time-varying signals at the corresponding pulse rate.

In the following, a more detailed description of processing physiological signals, in particular time-varying signals indicative of cardiac-synchronous motion of a subject will be explained with reference to the example of extracting signals indicative of a carotid displacement from the neck of a subject.

Advantageously, the side of the neck of the subject 100 is illuminated under and oblique angle by the first illumination unit 21 as indicated in FIG. 1. This condition can easily be met in practice and ensures that cardiac-related skin motion can be detected by a camera as the imaging unit 20 sensitive to minute brightness variations, most notably in the vicinity of pulsating arterial spots such as in the carotid artery (e.g., carotid sinus). For these particular spots the time-varying signal or cardiac-related skin motion signal, sMOT, as acquired by the camera in the vicinity of the carotid artery can be modeled as follows:

$$sMOT(t, \wp, f_{HR}^i) = f(D_{CA}(t, \wp)) + PPG_\lambda(t, \wp) + CM_{BCG}(t) + n(t, f_{HR}^i) \quad (1),$$

where the indices t, $\wp$ and $f_{HR}^i$ refer to temporal dependency, spatial variability (horizontal and vertical image plane), respectively. The quantity have $f_{HR}^i$ is defined as $f_{HR}^i = 1$. $f_{HR}^i < f_s/2$, with i $\in \mathbb{N}$, with $f_{HR}$ and $f_s$ being the pulse-rate and sampling frequencies, respectively) and narrows the scope of therefore mentioned equation to the cardiac-related frequency bands. The quantity $f(D_{CA})$ is a function, $f(\cdot)$, of the carotid artery displacement at the skin of the neck and is, in the given example, the desired time-varying signal indicative of cardiac-synchronous motion. Assuming $f(\cdot)$ to be linear is reasonable for neck motion signals as angular variations are within the order of 1 degree, though the subcutaneous fat tissue between the carotid wall and the skin surface signal are a likely source of signal damping, in particular for higher order harmonics. The contribution PPG), refers to interfering conditions from the (remote) PPG signal in the wavelength or camera channel at which data is acquired. It has been found that the PPG-waveform depends on the location and penetration depth of light. Therefore, it cannot be assumed that the PPG signal resembles the arterial dilation that is desired to be explored, and, consequently, it is preferably chosen to minimize its contribution. For example, a red color channel of the image data of the visible spectrum is used for evaluating motion since the relative PPG signal strength is lowest among the visible-to-infrared wavelength range.

Another interfering source that may be acknowledged is the common-mode ballistocardiographic motion denoted by ($CM_{BCG}$). The BCG signal propagates from the heart to the head and can be acquired by a camera even in subjects lying supine with neck support. BCG waveforms differ from arterial motion waveforms and are most pronounced under non-orthogonal illumination, e.g. near edges of the of the subjects outline. Filtering can be applied to filter out a common-mode contribution or common mode motion due to a respiration because it does not occur at the frequency of the cardiac-related variation of the time-varying signal of interest and can be removed by the extraction unit by optionally applying filtering. Lastly, the contribution $n(t, f_{HR}^i)$ may accounts for camera noise (white noise) and occasional involuntary movements such as swallowing, at the cardiac-related frequency bands. For convenience, the subscripts t, $\wp$ and $f_{HR}^i$ will be omitted in the following.

It has been found that under these conditions, joint interfering contributions from common mode BCG and PPG signals in the red channel of an RGB camera ($PPG_{red}$) are typically below an order of magnitude of the $D_{CA}$ related component acquired in the vicinity of the carotid artery. Consequently, it has been found that the acquired time-varying signal due to motion can be considered to have a dominant contribution to the sMOT signal, i.e., $sMOT \approx \kappa D_{CA} + n$, where $\kappa$ is an unknown gain factor which depends on actual arterial wall displacement, attenuation due to vessel-to-skin tissue and the gradient of the local lighting field.

In a further optional step ensemble-averaging can be performed, i.e. averaging waveforms for sMOT from a number of consecutive sMOT cardiac cycles, to provide an estimate for the carotid wall displacement waveform, $D_{CA}$, in arbitrary units. The carotid wall distention is related to the central pulse pressure (CPP) waveform. The value of the central pulse pressure (CPP) can also be demonstrated in the context of the laser Doppler velocimetry (LDV). The conversion of displacement to pressure can be done by applying suitable correction for non-linearity and hysteresis and may be achieved by an exponential or even tangent-based function and scaling of the foot-to-peak amplitudes of sMOT to brachial diastolic blood pressure (DBP) and systolic blood pressure (SBP), respectively. Non-linear models which assume a non-linear transfer function from displacement-to-pressure may more accurately translate vessel wall dynamics during each cardiac cycle.

Nonetheless it has been found that already the assumption of linearity between pressure and displacement waveforms yields that hysteresis effects are not too serious and that, advantageously, carotid arterial pressure-diameter relationship can be regarded as being linear. An advantage of this approach is that it simplifies the signal processing. In the following, a linear relationship is assumed. For simplicity, sMOT waveforms are presented on a normalized 0 to 1 basis or pressure-scaled.

In this context, FIG. 1 shows an embodiment of the system 1 for camera-based acquisition of carotid displacement waveforms from skin (micro)-motions (sMOT). During video recordings for acquisition of the image data the subject 100 sits on a chair with back and head support in a recumbent position wherein a back support with an angle of about 70 degrees with respect to the vertical plane is provided. In an experimental verification, subjects were instructed to look to the front or tilt their head rightwards such that the right side of their neck was exposed to the imaging unit 20 while breathing normally and avoiding voluntary movements during video recordings.

The image acquisition unit 20 can be regular RGB camera (e.g. global shutter RGB CCD camera USB UI-2230SE-C from IDS, with 500×500 pixels, 8 bit depth operating at a consent frame rate of 30 frames per second (fps). The image data can be stored in an uncompressed bit format for avoiding additional distortions due to compression techniques. The subject is illuminated as described above with a first illumination unit 21 for lateral illumination, thereby providing uneven illumination conditions and a second illumination unit 22 substantially parallel to the camera. In order to avoid distortions at the heart-rate frequency, the illumination units operated in AC-mode with a very high frequency around 22 kHz which is also high enough to prevent interference with the camera frame rate.

The first light source 21 is arranged to provide tangential illumination across the vicinity of the carotid sinus of the neck of the subject 100. This enhances visibility of the carotid artery pulsation (as minute brightness variations) on the camera sensor. Yet, lateral/uneven lighting conditions typically result in portions of the skin being under very low brightness (e.g., below 30 least significant values out of 255 of an 8 bit sensor), which would translate to sensor noise magnification on AC/DC normalized sMOT streams. To overcome this issue, a second illumination unit 22 can be placed frontally to the skin and perpendicular to the first light source to provide so-called filling light, i.e., to increase the average local brightness level and minimize the deleterious effects of sensor noise. In the arrangement shown in FIG. 1, the distances of the first illumination unit 21 to the neck of the subject 100 was about 30-50 cm and for the second illumination unit 22 the distance was 80-100 cm. In the present example, synchronized with the image acquisition, contact-based PPG signals (cPPG) were recorded in transmission mode at the index finger of the right hand (model CMS50E, Contec, China). Owing to a higher signal-to-noise-ration (SNR) then $D_{CA}$, cPPG signals can be used as a reference for probing the instantaneous pulse rate during video recordings and as a reference/template for computing the polarity of the time-varying signals obtained based on the image data. In the shown example, the right upper limp was supported on a rigid horizontal table 28 at the level of the heart.

Figure 5:
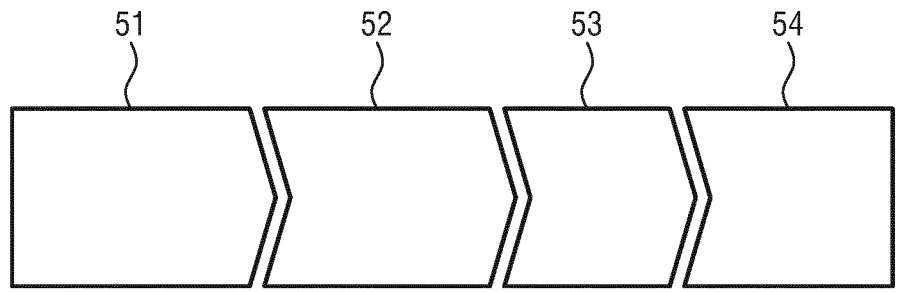
FIG. 5 shows an exemplary flow chart of processing steps.

FIG. 5 shows a diagram illustrating an exemplary processing pipeline or flow chart for processing the image data as acquired by the imaging unit 20. In a first preprocessing stage 51, an optional preprocessing step is performed for segmenting the image into valid skin pixels and non-skin pixels used for assembling a two-dimensional array of time-varying signals of sMOT-streams. Skin regions can be identified by known techniques such as manual selection, color-based skin identification or even based on PPG measurements. Optionally, the resolution of the image data provided by the camera can be reduced as explained below. The streams may be converted to a normalized AC/DC. Micro-motion maps of the 2D-strength of the pulsating skin can then be computed at based on a correlation of the time-varying signals with a signal indicative of a pulse of the subject, for example, as a complex inner-product between a cPPG waveform and individual sMOT-streams as the time-varying signals. These amplitudes maps can be used to guide the user at demarcating the suitable skin region of interest for querying the carotid artery displacement. Alternatively, automated selection can be performed by means of a selection unit. The signal from these regions of interest can then be ensemble-averaged and taken as an input for wave separation analysis, resulting in a decomposition of forward and reflected displacement waves for each of the measured signals. The ultimate outcomes are of the processing steps indicated in FIG. 5 are health parameters such as biomarker of cardiovascular (CDV) health, which can be exemplified with stiffness index (SI) and various potentially clinically relevant wave reflection parameters such as the augmentation pressure (AP, augmentation index (AIx) and reflection magnitude (RM).

A more detailed description of the processing steps shown in FIG. 5 will be provided hereinafter. Referring to the preprocessing step 51, first the image data or video frames (red channel, original size 500×500 pixels) are optionally blurred with an Gaussian kernel (box size, 45×45 pixels) to reduce the effect of sensor and quantization noise and subsequently resized by a factor of 1/5, resulting in images of size 100×100 pixels. The image data comprising a time sequence of image frames can be thought of as a three-dimensional data cube with two-dimensions for the horizontal, x, and vertical, y, frame coordinates and a dimension for discrete time, l=1 . . . L, where L is the length of the valid portion of the video recordings. Optionally, skin regions can be identified by pre-defined masks. Furthermore, in addition to the optional exclusion of non-skin pixels, overexposed sites and skin with very low brightness, for example due to being covered by body hair, can be excluded. In the present embodiment, each of the time-varying signals at valid skin coordinates (x, y) of the data cube is denoted as an sMOT stream. Optionally, a normalization step can be applied to limit the effect of brightness variations. The conversion can be achieved as follows:

$$sMOT_{AC/DC}(x, y, l) = \frac{sMOT_{Raw}(x, y, l) - sMOT_{LPF}(x, y, l)}{sMOT_{LPF}(x, y, l)},$$

where $sMOT_{LPF}$ (x,y) can be generated by optional low-pass filtering (LPF) of the sMOT signal, e.g. using a 9th order Butterworth IIR filter having a cutoff frequency of 30 Hz, with x, y=1 . . . 100 and l=1 . . . L. For convenience, the subscript AC/DC will be omitted in the following.

Figure 6:
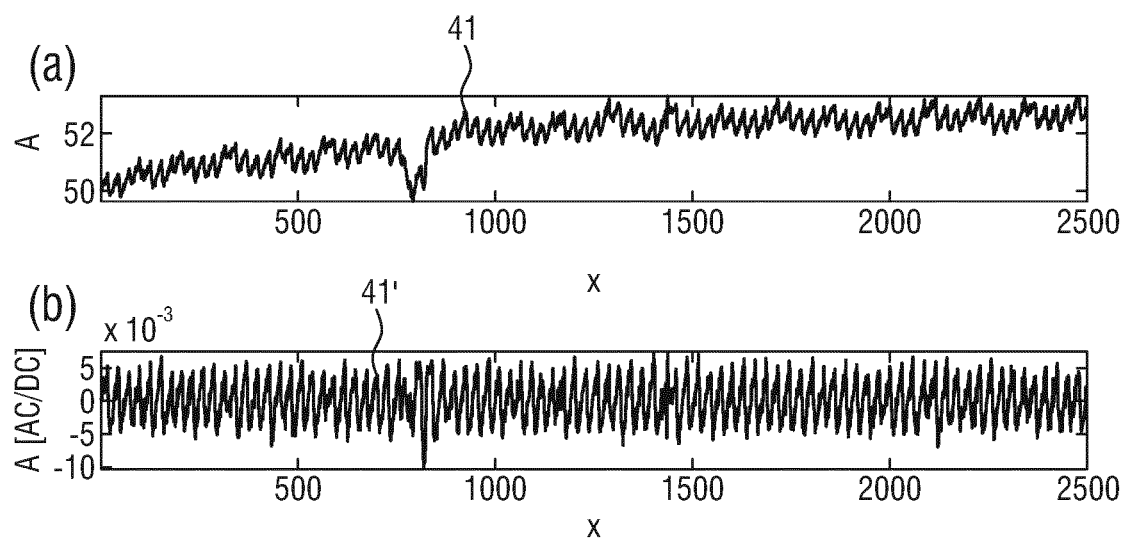
FIG. 6 shows diagrams illustrating a time-varying signal indicative of cardiac-synchronous motion.

FIG. 6 illustrates in the upper graph (a) an exemplary raw time-varying signal and in the lower graph (b) a normalized time-varying signal. The horizontal axis denotes samples x, whereas the vertical axis denotes the raw amplitude A or the normalized amplitude A[AC/DC], respectively. As can be seen from FIG. 6 (b) the amplitude of the time-varying sMOT signals are stabilized about the origin, while trends and low frequency drifts of the raw signal as shown in FIG. 6 (a) are ameliorated. Hence, the output of the preprocessing step 51 can be extracted time-varying signals indicative of cardiac-synchronous motion from the image data. Such extraction can be performed by the extraction unit 12 in FIG. 4.

FIG. 5 refers in a second step 52 to the mapping of relative strength of skin micro-motion. To minimize the effect of sensor noise of the imaging unit while retaining most of the energy within the time-varying sMOT signals, adaptive band-pass filtering (ABPF) can be applied. As a first step, the fundamental component of the pulse-rate frequency ($f_{HR}$)

can be determined based on the time-varying signals themselves or optionally based on an external signal as for example from a contact-PPG probe. In the given example segments of 256 taps are processed in an overlap-add scheme with 60% overlap and Hanning windowing. For each data segment, the pulse-rate was probed from the for example cPPG signal by peak detection.

Figure 7:
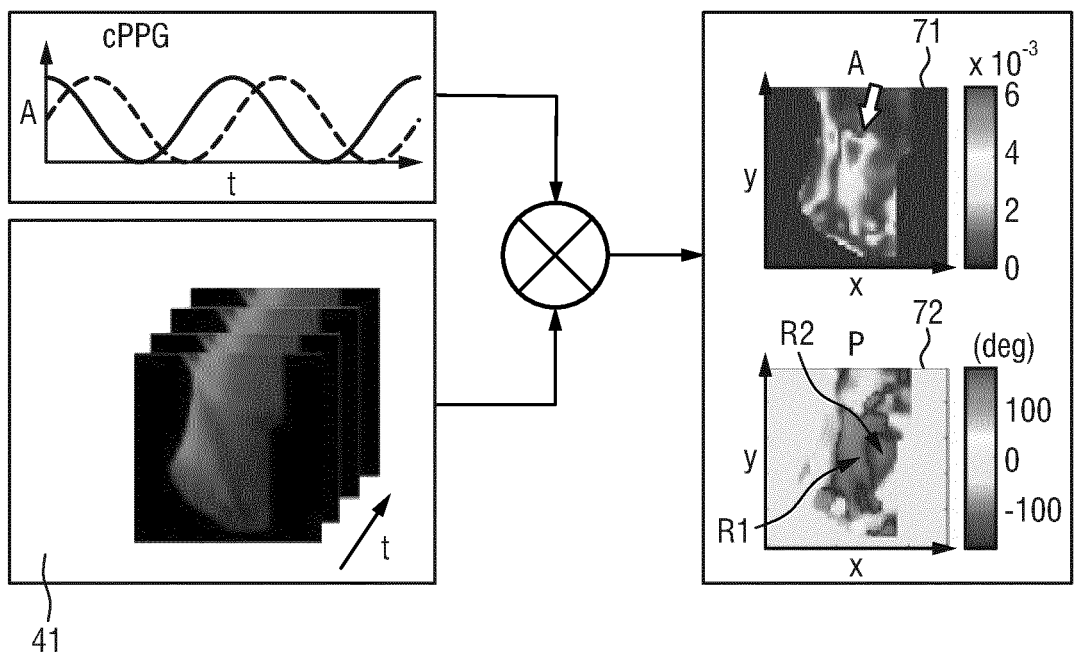
FIG. 7 shows an exemplary embodiment of determining a polarity of the time-varying signals.

FIG. 7 illustrates the determination of a polarity or phase φ and amplitude A of the time-varying signals indicative of the cardiac-synchronous (micro-) motion. The upper right graph in FIG. 7 illustrates an amplitude map 71 of the micro-motion signal. The arrow in the amplitude map 71 pointing to a hot spot in the amplitude map illustrates the location of a maximum motion of the carotid artery. It has been found that a carotid displacement signal $D_{CA}$ is typically strongest at the vicinity of arterial bifurcations (see FIG. 2, wherein the common carotid artery 106 separates into the internal carotid artery 102 and the external carotid artery 103.

The lower right graph illustrates a phase map 72 of the time varying signals for each of the pixels (x, y) of the image data. The amplitude map 71 and phase map 72 can be obtained by taking the time-varying signals for the individual pixels of the image data as a first input and a pulse signal, here taken from the contact-PPG probe (optionally filtered and Hilbert-transformed), cPPG, as a second input and taking the complex inner-product thereof. In other words, the complex inner-product from the data cube storing the spatially-varying sMOT signals 41 and the cPPG as a template signal for the inner product can be determined.

In the given example cPPG signal was Hilbert-transformed and normalized so that $\Sigma Re[\tilde{s}_{ref}]\tilde{s}_{ref} 1$, wherein Re(·) is the real operator and $\tilde{s}_{ref}$ is the normalized and Hilbert-transformed reference signal/template; i.e., $\tilde{s} = \sqrt{(C)hilb(cPPG)}$, with C being a real normalization constant. For each image coordinate (x, y), the outcome of the complex inner product between $\tilde{s}_{ref}(l)$ and each local sMOT (x, y, l), l=1 ... L is a complex number whose amplitude and phase results are illustrated in the corresponding amplitude map 71 and phase map 72 as shown in the right hand side of FIG. 7. As exemplified by the arrow in the amplitude map 71 in FIG. 7, the strongest intensity points is an sMOT image occur around the carotid sinus.

While the absolute phase only plays a secondary role in this disclosure, it can be used as tool for identifying signal inversions, i.e. for determining the polarity and polarity inversions (of around 180 degrees shifts in phase maps) in strongly pulsating spots. Phase inversion recommends caution when combining time-varying signals. Hence, instead of simply combining time-varying signals of strong amplitude, it is suggested to combine time-varying signals depending on their polarity to obtain a combination signal. Advantageously, the time-varying signals of the largest regions having same polarity can be combined to obtain the combination signal. Optionally, a selection unit for selecting a region of interest in the image frames of the image data, in particular as a region providing signals of same polarity and being adjacent to a region providing signals of opposite polarity indicated by regions R1 and R2, respectively. The combination unit can be further configured to combine time-varying signals from said region of interest, here region R1. Optionally, time-varying signals from region R2 can be inverted in polarity and also be combined with signals from region R1 to obtain a further strengthened combination signal.

It shall be understood that also alternative locations within the neck or sternal notch can be used or also different portions of the body such as a palm of the subject can be used for evaluation.

Figure 8:
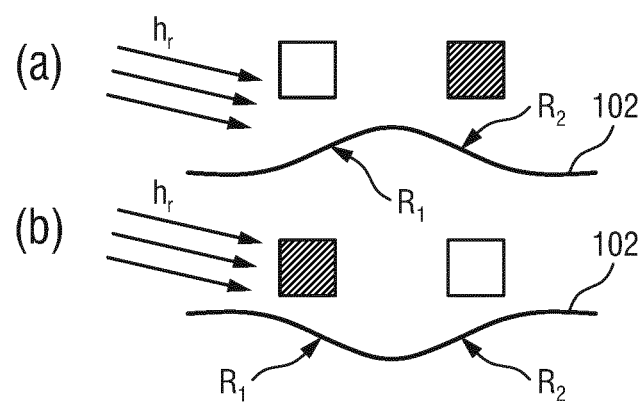
FIG. 8 shows a diagram illustrating regions of different motion-induced polarity.

FIG. 8 further illustrates the principle of neighboring regions having different polarity even though being affected by the same arterial micro-motion. In the upper graph FIG. 8 (a), the skin 102 of the subject shows an elevation whereas in the lower graph FIG. 8 (b) the skin 102 shows a dip. If light is falling onto the tissue under an oblique angle, i.e. as lateral illumination close to perpendicular (e.g. 45-85 degrees) to a surface normal of the skin, the region R1 on the left hand side will be brightly illuminated in FIG. 8 (a) wherein the region R2 on the right hand side is shaded and thus dark. On the other hand, as indicated in the lower graph FIG. 8 (b), if a dip is formed in the skin the lateral illumination does not illuminate the region R1 but instead provides bright illumination of region R2. A blood vessel such as the carotid artery located underneath the skin 102 of the subject 100 can thus lead to characteristic time-varying signals having opposite polarity but located closely adjacent to one another. It shall be understood that the curvature of the skin and the presence of a blood-vessel are not necessarily related. A curvature may generally be caused by any physiological structure.

Referring again to FIG. 5, in an optional next processing stage 53 robust ensemble-averaging (REA) can be performed to obtain a representative average displacement waveform from the image data, here in form of a video recording. Cardiac cycles can be demarcated in the time-varying signals and ensemble-averaging can be applied as a temporal super-resolution algorithm, i.e. combining a sufficiently large number of cardiac cycles ($N_c$, for example 200 cardiac cycles) to render sensor noise (zero mean, Gaussian distributed) negligible and also to delay with the relatively low temporal sampling rate here 30 Hz video frame rate. The cardiac cycles can be demarcated based on peak detection of the time-varying signals, an external (contact) PPG signal and/or based on frequency analysis of the time-varying signals. For improved robustness against sporadic interferences or non-representative cycles, for example ectopic beats or arrhythmia episodes, an optional confidence scheme can be applied for example for reducing motion artifacts whereby e.g. relative weights are assigned to individual cardiac cycles based on a trust metric or trust score derived from correlation with neighboring cycles. This aspect will also be described in more detail further below with a reference to FIG. 14.

Optionally, the time-varying signals indicative of cardiac-synchronous motion as processed herein can be resampled. For example the carotid artery displacement cycles can be registered to a temporal template of 35 samples per cardiac cycle. It has then found that at a s sampling rate of 30 Hz, setting the length of the temporal template to 35 samples per cardiac cycles is appropriate for typical cardiac cycles acquired at about 60-80 beats per minute (bpm). Based thereon, the robust ensemble averaging procedure can be expressed as follows:

$$D_{CA} = \frac{\sum_{n=1}^{N_c} \hat{d}_n w_n}{\sum_{n=1}^{N_c} w_n},$$

where $D_{CA}$ is measured and ensemble-averaged waveform for a given image data or video recording, $\hat{d}_n$ is the registered carotid displacement cycle and $w_n$ corresponding trust weights, n=1 . . . $N_c$.

The quality of the ensemble-averaged $D_{CA}$ waveforms can be assessed by using a signal-to-noise ratio (SNR) metric. For example the signal in the first 8 frequency bands (fundamental of pulse-rate frequency and its seven harmonics), for example on an FFT length of 256 per moving window. Hereby, the power of the true signal can be computed as the variance of the $D_{CA}$ cycle after adaptive band-pass filtering and spectral truncation to the first 8 cardiac frequency bands. For estimating a noise variance, it can be assumed that the noise level is similar in the vicinity of each cardiac-related frequency band so that the noise signal can be extracted in a bilateral neighborhood of two bins around each cardiac band. The power of the noise can be determined as the variance of the mean noise within each cardiac cycle. Optionally, a penalty of 0.64 (1.94 dB) can be applied to account for the ratio of 5 to 4 bins that were used for computing the signal and noise terms, respectively.

Referring again to FIG. 5, in the processing stage 54 health parameters are determined based on the (optionally ensemble averaged) combination signal by the analysis unit (15 in FIG. 4). As examples there are provided the stiffness index (SI) as a measure of large artery stiffness. SI is a ratio of the subject's height (h) over the temporal delay between forward and reflected waves ($TD_{fr}$):

$$SI=h/TD_{fr},$$

The formulation of SI translates the facts that (a) $TD_{fr}$ is the transit time of pressure waves from the route of the subclavian artery to the apparent side of reflection, and back to the subclavian artery, and (b) that this path length can be assumed to proportional to the subject's height (h). Therefore, SI is related to pulse wave velocity (PWV) and both can be expressed in units of linear velocity in m/s. By definition, due to the scaling, SI is invariant to the subject's height, which is a co-variant to waveform variability amongst subjects. From SI, one can arrive at the clinically relevant PWV by optionally further taking into account the complex impedance of the aorta bifurcation as reflection sides and optionally also age-dependency, resulting in an elusive elongation of the travel distance.

In addition or in the alternative one or more further parameters indicative of cardiovascular risk/health can be determined. For example, such parameters can aim to quantify the ratio between the amplitude of forward in reflected waves and/or its amplification effect on the actual pressure. Relevant examples are the augmentation index (AIx in [%]), as defined by $$AIx=(1-\max(D_f))\cdot 100(\%),$$

$$AP=AIx\cdot(SBP-DBP),$$

and reflection magnitude (RM in %) as given by $$RM = \frac{\max(D_b)}{\max(D_f)} \cdot 100(\%),$$

where $D_f$ and $D_b$ denote the forward and backward waveform decompositions of the measured $D_{CA}$ waveform. For providing AP, i.e. a pressure parameter, and being able to compute $D_f$ and $D_b$ morphological equivalence between the normalized pressure and displacement waveforms can be assumed, i.e., $D_{CA} \approx P_{CA}$. Hence, waveform separation (WSA) can be applied. While waveform separation analysis usually requires simultaneously acquired pressure and flow waveforms from a pulsating artery, it has been found that as replacement for the measured flow waveform a state-of-the-art template derived by Hametner et al. (Hametner et al., "Wave reflection quantification based on pressure waveforms alone—methods, comparison and clinical covariates", Comput. Methods Programs Biomed, 109, p. 250-259, 2013). This approach can be seen as based on physiological data and on a Windkessel (WK) model formulation.

Preferably, a WK-flow template can be provided for each subject and adjusted to the shoulder and the inflection point of the signal since it has been found that these characteristic points of the $D_{CA}$ waveforms correspond to the peak of the flow burst and to the end of systole, respectively. Finally, a complex impedance of the aorta can be determined to arrive at the forward and reflected components of the displacement waves. Details regarding the implementation of the WSA with the WK-flow template can be found further below.

Figure 9:
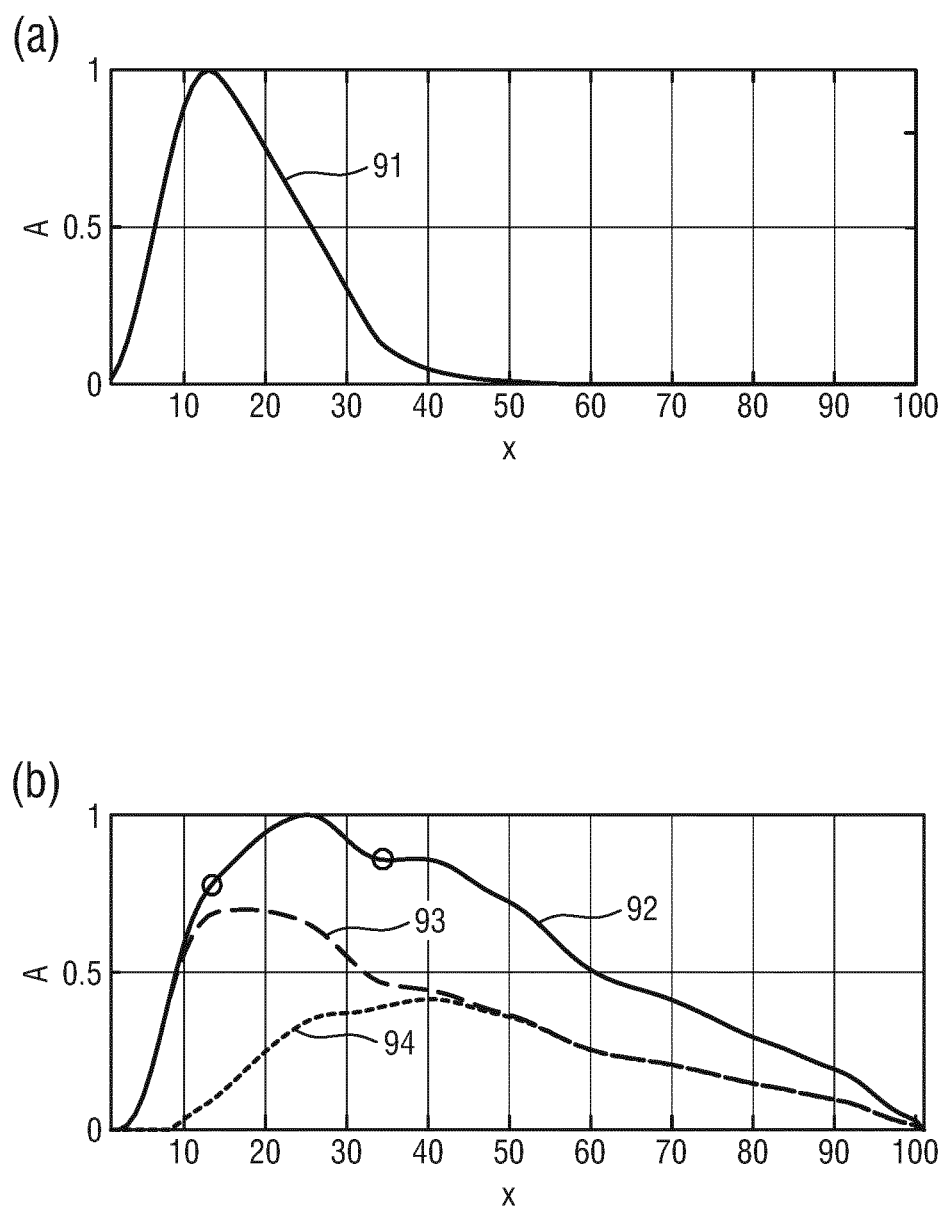
FIG. 9 shows a diagram illustrating waveform component analysis.

FIG. 9 illustrates the waveform separation analysis (WSA) procedure. FIG. 9(a) displays a fitted WK-flow template 91. The horizontal axis denotes normalized samples x, whereas the vertical axis denotes the amplitude A. FIG. 9(b) illustrates a carotid displacement waveform $D_{CA}$ 92 as an exemplary time-varying signal indicative of cardiac synchronous motion extracted from the image data. The measured $D_{CA}$ waveform 92 is represented with its constituting corresponding forward decomposition $D_f$ 93 and the corresponding backward decomposition $D_w$ 94. Waveforms given in FIG. 9 are normalized to 100 samples per cardiac cycle. The amplitude of the WK-flow and $D_{CA}$ are normalized to unity while $D_f$ and $D_b$ are expressed as a fraction of $D_{CA}$. For extracting stiffness and reflection parameters, the obtained displacement waveforms 92 needs to be decomposed into forward and backward waveforms as illustrated in FIG. 9 (b). It has been found that algorithms described in literature for decomposing pressure waves can also be applied to displacement waveforms indicative of cardiac-synchronous motion as used herein. In particular for the carotid artery the morphology of the measured displacement waveform can be approximated to resemble the pressure waveform.

Referring again to FIG. 9, the displacement signal was first upsampled per cardiac cycle and smoothed using Savitzky-Golay filtering (third order, 7-tap Hanning window). It has been found that such optional preprocessing resulted in an improvement in temporal resolution and better conditioning of the signals for subsequent calculating of higher order derivatives. The waveform separation analysis can be performed by the impedance method disclosed by Hughes et al., "Forward and backward waves in the arterial system: Impedance or wave intensity analysis", Med. Biol. Eng. Comput. 47: p. 207-210, 2009. By using Hametner's Windkessel-based (WK) model, it is possible to perform the procedure for the displacement waveforms alone. For each measured displacement waveform, $D_m$ the WK template for the flow, $Q_{WK}$ can be scaled to match the inflection points corresponding to the peak and end of systole. These points are denoted by the first and second circles in FIG. 9 (b) on trace 92, respectively. The characteristic points can be determined by inspecting the zero crossings or peaks of higher order derivatives such as the fourth order of the peak of systole and compound second and third order for the end of systole. Furthermore, the (complex) impedance parameter, $\tilde{Z}_c$, can be computed by averaging the fourth and fifth harmonics of ratio $FFT[P_m](j\omega)/FFT[Q_{WK}](j\omega)$, where the FFT[·] denotes conversion to the Fourier domain. Since it has been found that most of the displacement energy is concentrated in the first 5 harmonics, a proposed procedure shows advantageous error characteristics even though being truncated. Based on $\tilde{Z}_c$, wave separation analysis into forward and reflected waveforms can be performed as follows:

$$D_f = (D_m + Z_c Q_{WK})/2,$$

$$D_b = (D_m - Z_c Q_{WK})/2 = P_m - P_f,$$

Figure 10:
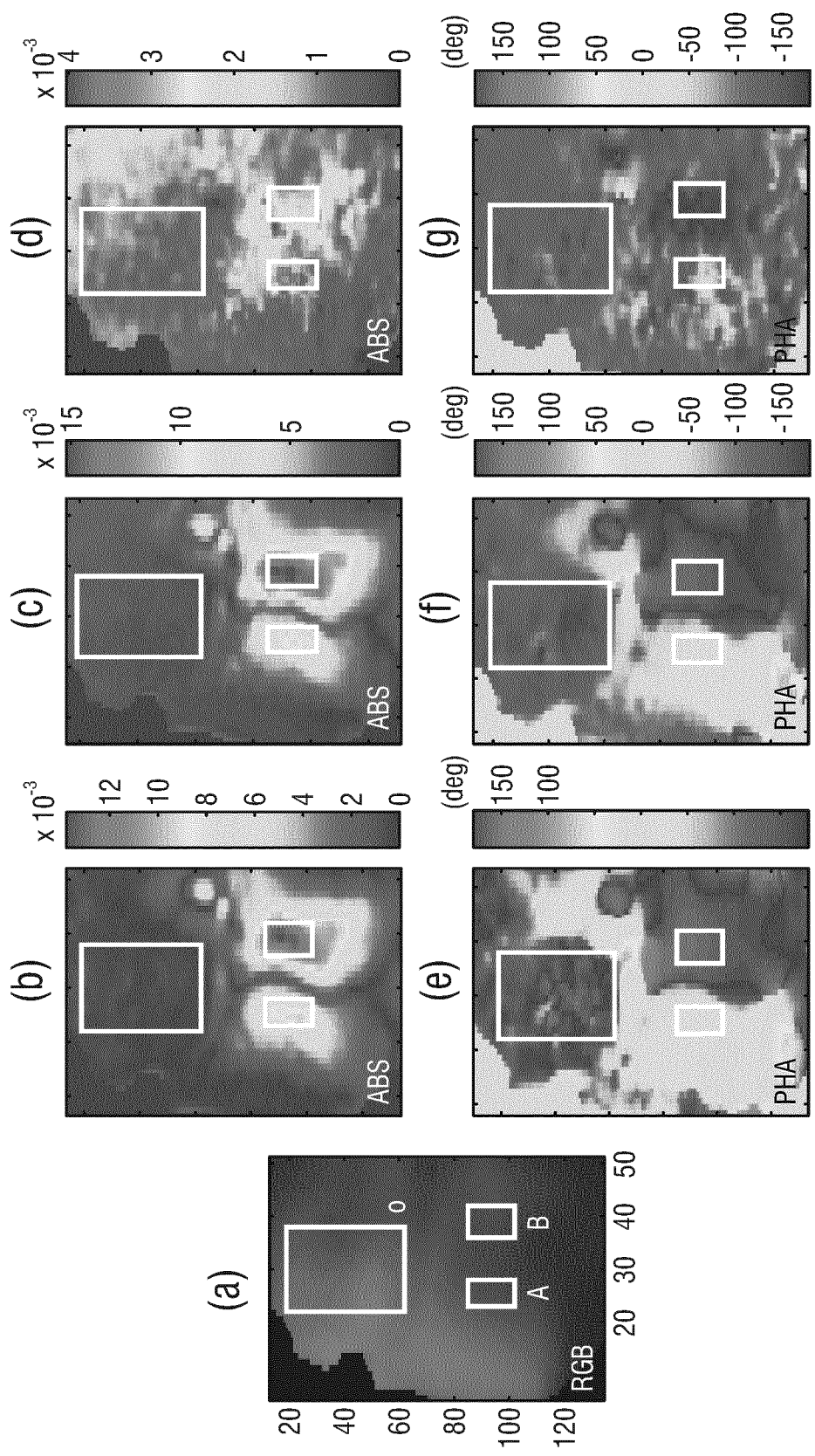
FIG. 10 shows diagrams of the acquired image data as well as an absolute value and phase of the time-varying signals in different color channels.

FIG. 10 shows an exemplary diagram exemplifying the extraction of a time-varying signal indicative of cardiac-synchronous motion, for example of a carotid displacement waveform. FIG. 10(a) illustrates the neck of the subject being recorded under uneven illumination as acquired by the measurement setup shown in FIG. 1 wherein the first illumination unit 21 provides a lateral illumination. The remaining figures are amplitude maps (b)-(d) and phase maps (e)-(g) for the normalized red, normalized green and normalized green minus normalized red (Gn-Rn) time-varying signals. As shown in FIG. 10(a) two neighboring regions of interest A and B are defined such that the $D_{CA}$ signals had maximum strength and were in counter phase, i.e. having opposite polarity. As explained above with reference to FIG. 8, the polarity can depend on the orientation of the skin surface with respect to the main light source (see illumination unit 21 in FIG. 1).

In the given examples, the regions A and B are selected to have a predetermined size and are located so as to include the pixels having maximum amplitude as e.g. apparent from FIG. 10(b) and at the same time providing opposite polarity as indicated in FIG. 10(e). Alternatively, the selection unit can be configured to select e.g. all pixels having same polarity for one region of interest, selecting the regions of interest so as to include signals above a predetermined relative or absolute amplitude threshold; and/or pixels of opposite polarity being separated from each other by no more than a predetermined spatial distance within the image frame. The selection unit can be configured to select time-varying signals corresponding to a region of interest (ROI) in the image frames of the image data from pixels (locations) with a (relatively) high amplitude, or within a certain percentage from a maximum amplitude, optionally from a maximum amplitude that occurs in a region selected in a previous selection step. Alternative and/or additional selection criteria comprise pixels above a minimum illumination level, not too close to the clipping level, preference for relatively smooth (no texture) regions, etc. An optional further region of interest indicated by O is shown in FIG. 10(a) which corresponds to a cheek of the subject. As can be seen from FIG. 10(b) the signal amplitude at the cheek in this red channel is at least an order of magnitude below the carotid artery displacement amplitude of regions of interest A and B. Hence, a PPG impact in the red channel is about an order of magnitude lower than the displacement waveform. It has been found that the same observation is not guaranteed for signals extracted from the green channel as shown in FIG. 10(c) or involving channel combinations such as green-red as shown in FIG. 10(d) since the PPG-related contributions therein are higher.

In a refinement, also time-varying signals indicative of cardiac-synchronous motion having different polarity can be combined by setting the convention that the systolic slope to be positive and flipping the time-varying signals accordingly, for example inverting the signal from region of interest B.

Figure 11:
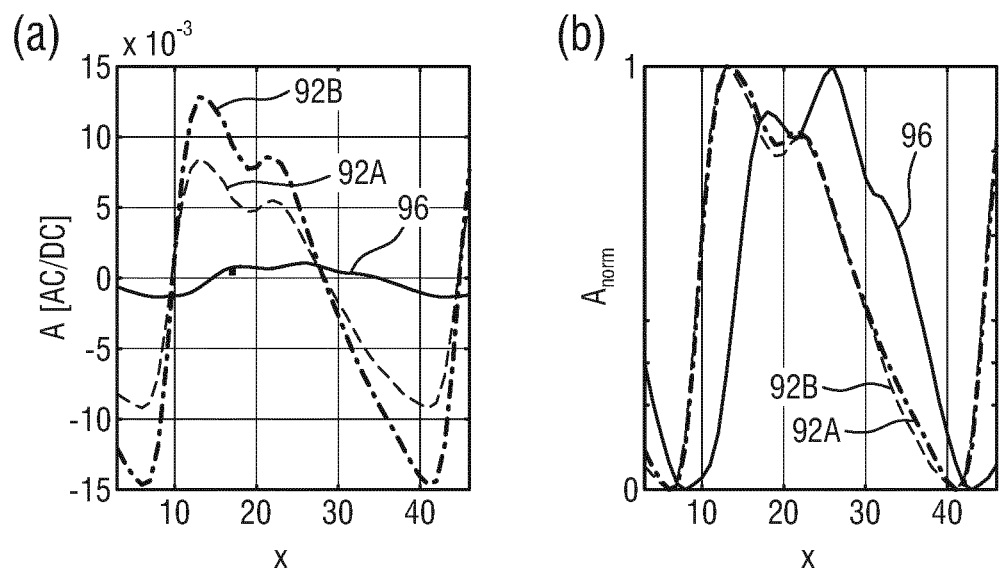
FIG. 11 shows a further example of time-varying signals.

FIG. 11 shows the respective sign-corrected signals from regions of interest A (signal 92A), B (signal 92B) and O (signal 96). The correspondence of signal 92A and 92B shows that the shape of the carotid displacement waveform ($D_{CA}$) is unaffected by the polarity of the time-varying signal. Nevertheless, the signal quality can be improved by selecting the strongest-amplitude time-varying signal. FIG. 11 further illustrates that the PPG signal 96 is different with respect to the motion induced displacement signals. Rather than reflecting the status of the large vessels, the PPG signal results from the propagation of the pressure wave into the micro-vascular bed of tissue. Indeed, the high resistance offered by the arterioles and capillary loops (characterized by relatively small diameter and much higher rigidity) to flow/pressure wave causes signal damping and leakage of higher frequency contact and waveforms.

In the given example, the signals 92A and 92B are extracted from the red channel which is only to a limited extent contaminated by PPG signals. The PPG signal 96 shown in FIG. 11 is derived from the green color channel which shows a strong PPG amplitude. The signal in FIG. 11(b) has been normalized to unit amplitude (0-1) to illustrate the different morphology of the displacement signals 92A, 92B on the one hand and the PPG signal 96 on the other hand.

Figure 12:
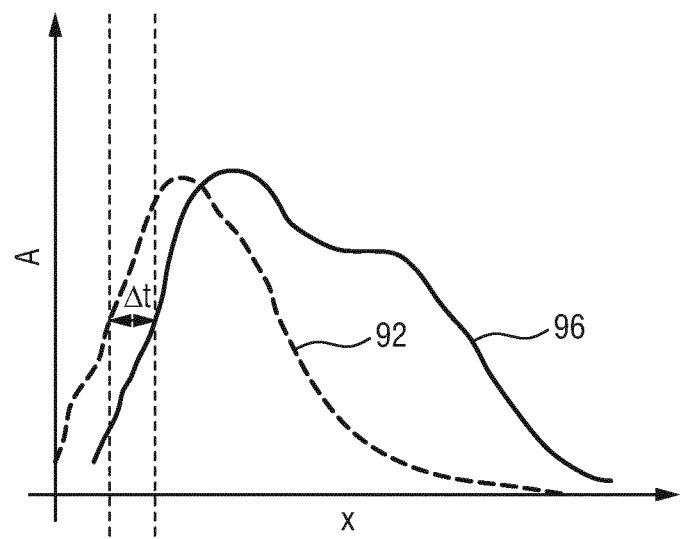
FIG. 12 shows a diagram illustrating the relationship between a PPG-signal and a time-varying signal indicative of a cardiac-synchronous motion.

FIG. 12 shows a second diagram illustrating the different morphology and timing of a motion-induced displacement signal 92 and a PPG signal 96. The horizontal axis denotes the samples x (or time t respectively), whereas the vertical axis denotes the signal amplitude A. In an embodiment the analysis unit can be configured to derive the health parameter based on the motion-based combination signal and an absorption-based PPG signal 96, in particular based on a transfer function between the motion-based combination signal and the PPG signal.

In an embodiment, the aspect of determining a polarity and combining signals depending on their polarity can be advantageous but optional. Hence, according to a further aspect, a device for processing physiological signals of a subject can be provided comprising an input unit for obtaining (a) a first signal indicative of cardiac-synchronous motion and (b) a second signal indicative of an absorption (PPG); and an analysis unit configured to determine a health parameter based on a relation between said motion-based first signal and said absorption-based second signal. In particular, a device for processing physiological signals of a subject can be provided comprising an input unit for obtaining (a) a first signal indicative of cardiac-synchronous motion and (b) a second signal indicative of an absorption (PPG); and a processing unit configured to determine a transfer function between the motion-based first signal and the absorption-based second signal; and an analysis unit for determining a health parameter based on said transfer function. Hence, the relation can be a transfer function between the first signal and the second signal and the health parameter can be determined based on said transfer function. In other words, it is proposed to determine a (vascular) health parameter based on a transfer function between a motion-based signal and an absorption-based signal. The respective signals can be obtained as described above.

In an embodiment the transfer function can be indicative of a blood transport from an artery to arterioles and/or capillaries. Referring again to FIG. 12, the health parameter can be derived based on a time difference Δt between the displacement signal 92 and the PPG signal 96. In addition or in the alternative, the analysis unit can be configured to derive a health parameter based on one or more morphology parameters of the displacement signal 92 and the PPG signal 96. The analysis unit can be configured to determine a health parameter indicative of a vascular state based on one or more features of said transfer function such as a relative gain at a particular frequency compared to another frequency, a phase shift, a time difference at different frequencies including DC.

The transfer function can be referred to as a mathematical function relating to an output (for example the PPG signal 96) or response of a system such as filter circuit to the input or stimulus (here provided as the displacement signal 92) between (i) an input motion-derived, pulse-pressure waveform near a superficial artery given herein by the waveform 92, and (ii) an output absorption-derived pulse-waveform (PPG) from a neighboring skin-side being less effected by motion. For example the first input signal can be a signal acquired in the vicinity of the carotid artery, whereas the second PPG signal is derived from a cheek of the subject. Also in this aspect the proposed illumination, in particular having illumination units as arranged as shown in FIG. 1 and by selecting the wavelength of the light emitted by the first and/or second illumination units as described above.

Figure 13:
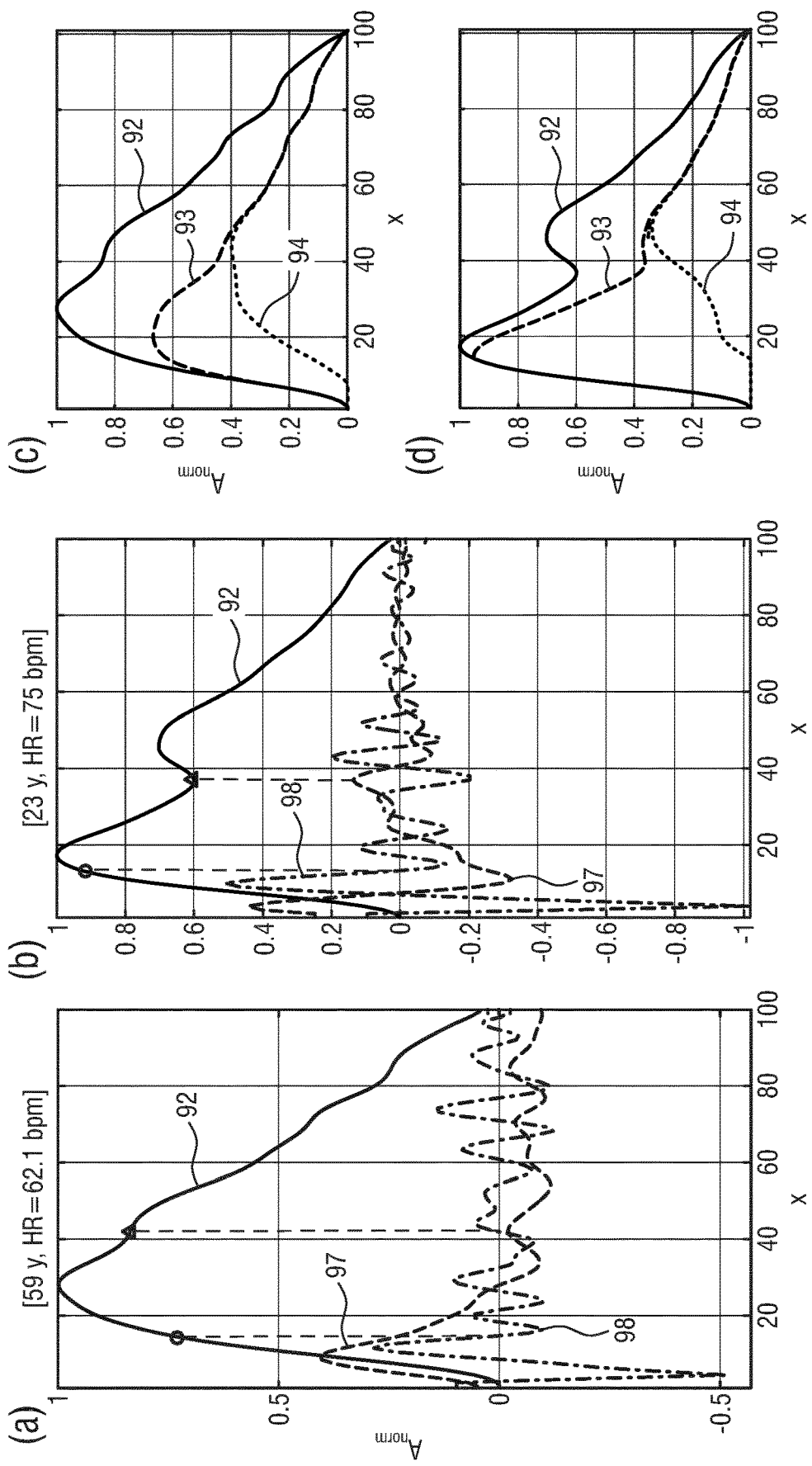
FIG. 13 shows diagrams illustrating steps of the waveform processing.

FIG. 13 shows a diagram illustrating the waveform separation analysis (WSA) in more detail. Waveform separation analysis for the displacement waveform 92, as an exemplary time-varying signal indicative of cardiac-synchronous motion, in an embodiment requires the detection of critical points for the peak an end of flow to be estimated using higher order derivatives. Based thereon, the WK-based flow template as introduced above with reference to FIG. 9 for the displacement waveform for each subject can be adjusted.

FIG. 13 illustrates the procedure of waveform separation analysis for two exemplary subjects. The displacement waveform is denoted by 92, its second order derivative by 97 and its fourth order derivative by 98. The criteria of finding the first zero crossing of the fourth order derivative 98 and the relative maximum of the second order derivative 97 of the displacement waveform 92 allow automated detection of the instance of the peak and end of the systolic flow, respectively.

FIGS. 13(c) and (d) show a decomposition of the displacement signal 92 into the forward displacement wave $D_f$ 93 and the backward reflected wave $D_b$ 94. A significantly different waveform can be seen for the two different subjects. The waveform in FIG. 13(c) is taken from a 59 year old male whereas the waveform in FIG. 13(d) was taken from a 23 year old male. The comparison of those figures suggests a more prominent contribution of the reflected wave as a function of aging.

Furthermore, it was found that the arterial stiffness as given by the stiffness index (SI), augmentation index (AIx), augmentation pressure (AP), reflection magnitude (RM) were strongly correlated with increasing age. On the other hand, the average heartrate (HR) was inversely correlated with age.

Advantageously, the analysis unit can be further configured to take such correlations into account when determining a health parameter for a subject, for example by determining an arterial stiffness of the subject as compared to a peer group of given age.

Figure 14:
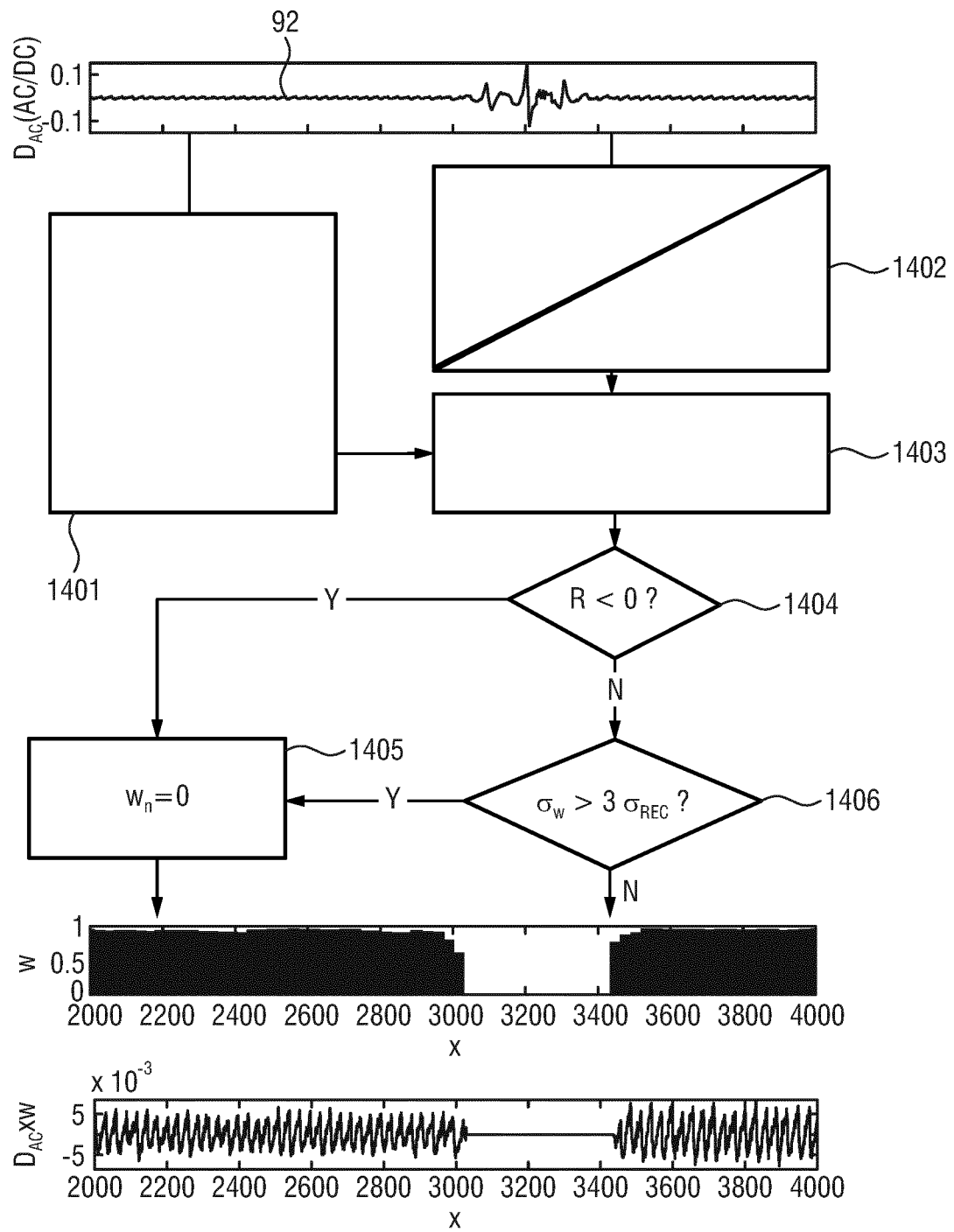
FIG. 14 shows a diagram indicating the reduction of motion artifacts.

FIG. 14 illustrates a diagram of an exemplary procedure for motion artifacts reduction. Motion artifacts as used herein refers artifacts due to large-scale involuntary motion of the subject such as swallowing and large scale motions of the body such as repositioning the neck. Thereby, the motion artifact reduction procedure aims to ensure that the time-varying signal indicative of cardiac-synchronous motion, here a displacement waveform of the carotid artery $D_{CA}$, are artifact-robust against, e.g. sudden body motions and swallowing. The proposed approach is based on weighted averaging and relies on three major assumptions: (1) the artifacts and the cardiac cycles are uncorrelated; (2) the artifacts have higher amplitude than the time-varying signals; (3) the corrupted portions of the time-varying signals do not affect more than half of the total recorded cardiac cycles. In an embodiment, it is thus proposed to define trust weights w as the positive Pearson correlation coefficients between a window of cardiac correlation coefficients between a window of cardiac cycles and the median cycle of the $D_{CA}$ signal (AC/DC-normalized).

This approach is illustrated in FIG. 14, wherein the $D_{CA}$ signal is taken as an input. Based thereon, L consecutive cardiac cycles are extracted in step 1401. They can be previously scaled to a predetermined number of samples per cycle. In a parallel step 1402 a median signal value for the cycle and for the recording can be calculated and a template can be generated based thereon for one cardiac cycles. In step 1403 a correlation coefficient between the template obtained from step 1402 and the respective individual cycles obtained from step 1401 can be estimated. As indicated by the decision step 1404 the trust weight w for sample n is set to zero in step 1405 if the correlation coefficient is negative. Furthermore, if the standard deviation σw of the window surrounding the cardiac cycles under evaluation, σw, is determined to be an outlier, for example is larger than three times the standard deviation of the median $D_{CA}$ cycle, denoted as $\sigma_{REC}$ in a decision step 1406 is also truncated to zero in step 1405.

The lower graphs in FIG. 14 illustrate the trust weights w and the resulting weighted displacement waveform signal $D_{CA} \cdot xw$. As can be seen from the given example, the incoming time-varying $D_{CA}$ signal is polluted by a strong motion artifact between samples 3000 and 3400. The shown procedure allows artifact suppression by simple element-multiplication of the trust metric w with the extracted time-varying signal indicative of cardiac synchronous motion, here $D_{CA}$.

In the present disclosure a device for processing physiological signals of the subject is presented that extracts time-varying signals indicative of cardiac-synchronous (vascular) motion from image data comprising a time sequence of image frames of a scene. The time-varying signals can be indicative of a vascular motion such as carotid displacement signal obtained from the skin of the neck of a subject. The approach is in clear contrast with the PPG-imaging literature. So far, remotely acquired motion-signals have been regarded as artifacts to actual remote-PPG signals. While PPG signal processing is confined to remote pulse-rate extraction (and optionally blood oxygen saturation measurement), the analysis unit proposed herein can be configured to evaluate a morphology of the (combined) time-varying signal to determine a (vascular) health parameter.

It has been found that signals indicative of cardiac-synchronous (vascular) motion are promising for cardiovascular health assessment in an unobtrusive way. Furthermore, the proposed device and system are easier to handle than systems based on laser Doppler velocimetry (LDV), tonometry and oscillometric methods. Furthermore, shape deformations of between PPG signals and displacement signals can be evaluated for example by means of evaluating a transfer function and deriving (vascular) health parameters based thereon.

A further advantage of the proposed method is that not only a single site can be probed but that a plurality of time-varying signals can be combined such that the reliability is improved. By further taking in account the polarity of the signals it is ensured that the resulting signal-to-noise ratio can be improved instead of having the detrimental effect of counter phase or counter polarity signals cancelling out one another.

It shall be understood that one or more of the aspects of (a) determining a polarity and combining the respective time-varying signals; (b) the arrangement of a first and/or second illumination unit, in particular the aspect of providing oblique illumination; (c) wavelength selection for the first and/or second illumination unit; and (d) evaluating a transfer function between a motion-based signal and an absorption based signal can advantageously be combined but may also be used separately.

An advantage of evaluating time-varying signals indicative of cardiac synchronous motion, such as a carotid displacement waveform, is that they have been found to be a reliable indicator for deriving a (vascular) health parameter whereas PPG signals have been found to be less reliable for deriving central biomarkers of vascular health since the micro-vasculature of the superficial tissue which causes the absorption of light to be evaluated by PPG deforms the shape of the original pulse wave in the major blood vessels and is thus an indicator of reduced reliability.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

Means plus function language, such as means for . . . , shall in particular refer to means adapted to or configured to perform the given function. For example, an analysis unit for determining a health parameter may refer to an analysis unit adapted to or configured to determine the health parameter.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. Device for processing physiological signals of a subject comprising:
   an input interface to obtain image data of a scene, said image data comprising a time sequence of image frames;
   an extraction unit to extract time-varying signals indicative of cardiac-synchronous motion from a red and blue color channel while bypassing usage of a green color channel of said image data, wherein said time-varying signals are motion signals indicative of a vascular micro-motion indicative of a vascular displacement waveform;
   a polarity determination unit to determine a polarity of the time-varying signals, wherein the polarity corresponds to a phase of the time-varying signals;
   a combination unit to combine time-varying signals depending on their polarity to obtain a combination signal; and
   an analysis unit to determine a health parameter based on the combination signal, wherein the health parameter is a vascular health parameter comprising an augmentation pressure, an augmentation index, a reflection magnitude, and a stiffness index; wherein the augmentation index is defined by $AIx=(1-max(Df))*100(\%)$, wherein Df and Db denote forward and backward waveform decompositions of a time-varying signal indicative of a carotid displacement waveform DCA; and wherein the augmentation pressure is defined by $AP=AIx*(SBP-DBP)$, wherein SBP denotes Systolic Blood Pressure and DPB denotes Diastolic Blood Pressure.

2. Device as claimed in claim 1, further comprising a selection unit to select time-varying signals corresponding to a region of interest (ROI) in the image frames of the image data, wherein the selection unit is configured to select the region of interest as a region providing signals of same polarity and being adjacent to a region providing time-varying signals of opposite polarity; and wherein the combination unit is further configured to combine said selected time-varying signals from said region of interest.

3. Device as claimed in claim 1, wherein the polarity determination unit is configured to correlate the time-varying signals with a signal indicative of a pulse of the subject.

4. Device as claimed in claim 3, wherein the signal indicative of a pulse of the subject is derived from a photoplethysmographic (PPG) signal or an electrocardiographic (ECG) signal.

5. Device as claimed in claim 1, wherein the analysis unit configured to derive the health parameter based on the combination signal and an absorption-based photoplethysmographic (PPG) signal.

6. Device as claimed in claim 5, wherein the analysis unit is configured to derive the health parameter based on a transfer function between the combination signal and the photoplethysmographic (PPG) signal.

7. System for monitoring a health parameter of a subject, the system comprising:
   an imaging unit to acquire image data of a scene; and
   a device to process physiological signals of a subject as defined in claim 1 based on the acquired image data of the scene.

8. System as claimed in claim 7, further comprising an illumination unit, wherein the illumination unit and the imaging unit are arranged such that an angle φ between light emitted by the illumination unit and light received by the imaging unit is $|\varphi|\geq 45°$.

9. System as claimed in claim 8, further comprising a second illumination unit, wherein the second illumination unit and the imaging unit are arranged such that an angle θ between light emitted by the second illumination unit and light being received by the imaging unit is $|\theta|\leq 30°$.

10. System as claimed in claim 9, wherein the second illumination unit is configured to emit light at a second wavelength providing high absorption in blood, in particular a wavelength between 500 nm and 610 nm.

11. System as claimed in claim 9, wherein the second illumination unit and the imaging unit are arranged such that the angle θ between light emitted by the second illumination unit and light being received by the imaging unit is $|\theta|\leq 20°$.

12. System as claimed in claim 8, wherein the illumination unit is configured to emit light at a first wavelength providing low absorption in blood and/or providing a shallow skin penetration depth.

13. System as claimed in claim 12, wherein the illumination unit is configured to emit light at a wavelength shorter than 500 nm or longer than 610 nm.

14. System as claimed in claim 8, wherein the illumination unit and the imaging unit are arranged such that the angle φ between light emitted by the illumination unit and light received by the imaging unit is |φ|≥60°.

15. Device as claimed in claim 1, wherein the vascular health parameter further comprises a stiffness index and a reflection magnitude; and wherein the reflection magnitude is defined by $$RM = \frac{\max(D_b)}{\max(D_f)} \cdot 100(\%),$$

16. Method for processing physiological signals of a subject, the method comprising:
- obtaining image data of a scene, said image data comprising a time sequence of image frames;
- extracting time-varying signals indicative of cardiac-synchronous motion from a red and blue color channel while bypassing usage of a green color channel of said image data, wherein said time-varying signals are motion signals indicative of a vascular micro-motion indicative of a vascular displacement waveform;
- determining a polarity of the time-varying signals, wherein the polarity corresponds to a phase of the time-varying signals;
- combining time-varying signals depending on their polarity to obtain a combination signal; and
- determining a health parameter based on the combination signal, wherein the health parameter is a vascular health parameter comprising an augmentation pressure, an augmentation index, a reflection magnitude, and a stiffness index; wherein the augmentation index is defined by AIx=(1−max(D))*100(%), wherein Df and Db denote forward and backward waveform decompositions of a time-varying signal indicative of a carotid displacement waveform DCA; and wherein the augmentation pressure is defined by AP=AIx*(SBP−DBP), wherein SBP denotes Systolic Blood Pressure and DPB denotes Diastolic Blood Pressure.

17. At least one non-transitory computer readable medium, comprising a set of instructions, which when executed by a computing device cause the computing device to:
- obtain image data of a scene, said image data comprising a time sequence of image frames;
- extract time-varying signals indicative of cardiac-synchronous motion from a red and blue color channel while bypassing usage of a green color channel of said image data, wherein said time-varying signals are motion signals indicative of a vascular micro-motion indicative of a vascular displacement waveform;
- determine a polarity of the time-varying signals, wherein the polarity corresponds to a phase of the time-varying signals;
- combine time-varying signals depending on their polarity to obtain a combination signal; and
- determine a health parameter based on the combination signal, wherein the health parameter is a vascular health parameter comprising an augmentation pressure, an augmentation index, a reflection magnitude, and a stiffness index; wherein the augmentation index is defined by AIx=(1−max(D))*100(%), wherein Df and Db denote forward and backward waveform decompositions of a time-varying signal indicative of a carotid displacement waveform DCA; and wherein the augmentation pressure is defined by AP=AIx*(SBP−DBP), wherein SBP denotes Systolic Blood Pressure and DPB denotes Diastolic Blood Pressure.

* * * * *